(12) United States Patent
Fallin et al.

(10) Patent No.: US 10,820,918 B2
(45) Date of Patent: Nov. 3, 2020

(54) TRANSOSSEOUS GUIDE AND METHOD

(71) Applicant: Crossroads Extremity Systems, LLC, Memphis, TN (US)

(72) Inventors: T. Wade Fallin, Hyde Park, UT (US); Joel Helgerson, Erie, CO (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 142 days.

(21) Appl. No.: 15/887,095

(22) Filed: Feb. 2, 2018

(65) Prior Publication Data
US 2018/0153566 A1    Jun. 7, 2018

Related U.S. Application Data

(63) Continuation-in-part of application No. 15/211,673, filed on Jul. 15, 2016, now Pat. No. 10,154,868, and a continuation-in-part of application No. 15/211,764, filed on Jul. 15, 2016, now Pat. No. 10,258,401.

(60) Provisional application No. 62/193,888, filed on Jul. 17, 2015.

(51) Int. Cl.
| A61B 17/17 | (2006.01) |
| A61B 17/04 | (2006.01) |
| A61B 17/88 | (2006.01) |
| A61B 17/16 | (2006.01) |

(52) U.S. Cl.
CPC ...... *A61B 17/1796* (2013.01); *A61B 17/0469* (2013.01); *A61B 17/0482* (2013.01); *A61B 17/1697* (2013.01); *A61B 17/1714* (2013.01); *A61B 17/1778* (2016.11); *A61B 17/8861* (2013.01); *A61B 17/0401* (2013.01); *A61B 17/0485* (2013.01)

(58) Field of Classification Search
CPC ............ A61B 17/1796; A61B 17/1778; A61B 17/0469; A61B 17/0482; A61B 17/1697; A61B 17/1714; A61B 17/8861
See application file for complete search history.

(56) References Cited

U.S. PATENT DOCUMENTS

| | | | |
|---|---|---|---|
| 2007/0005067 A1* | 1/2007 | Dross | A61B 17/0483 606/232 |
| 2010/0106194 A1* | 4/2010 | Bonutti | A61B 17/17 606/279 |
| 2011/0009867 A1* | 1/2011 | Oren | A61B 17/0485 606/80 |
| 2011/0295279 A1* | 12/2011 | Stone | A61B 17/0469 606/145 |
| 2013/0123840 A1* | 5/2013 | Murphy | A61B 17/0469 606/228 |
| 2016/0015380 A1* | 1/2016 | Sholev | A61B 17/0482 606/80 |
| 2017/0014172 A1* | 1/2017 | Fallin | A61B 17/1778 |
| 2018/0078251 A1* | 3/2018 | Copple | A61B 17/0469 |

* cited by examiner

*Primary Examiner* — Tessa M Matthews
(74) *Attorney, Agent, or Firm* — David Meibos; Maywood IP Law

(57) ABSTRACT

Instruments and methods for surgical transosseous attachment to a bone include a guide able to guide the formation of intersecting bone tunnels and a passer able to pass a member through the bone tunnels.

20 Claims, 29 Drawing Sheets

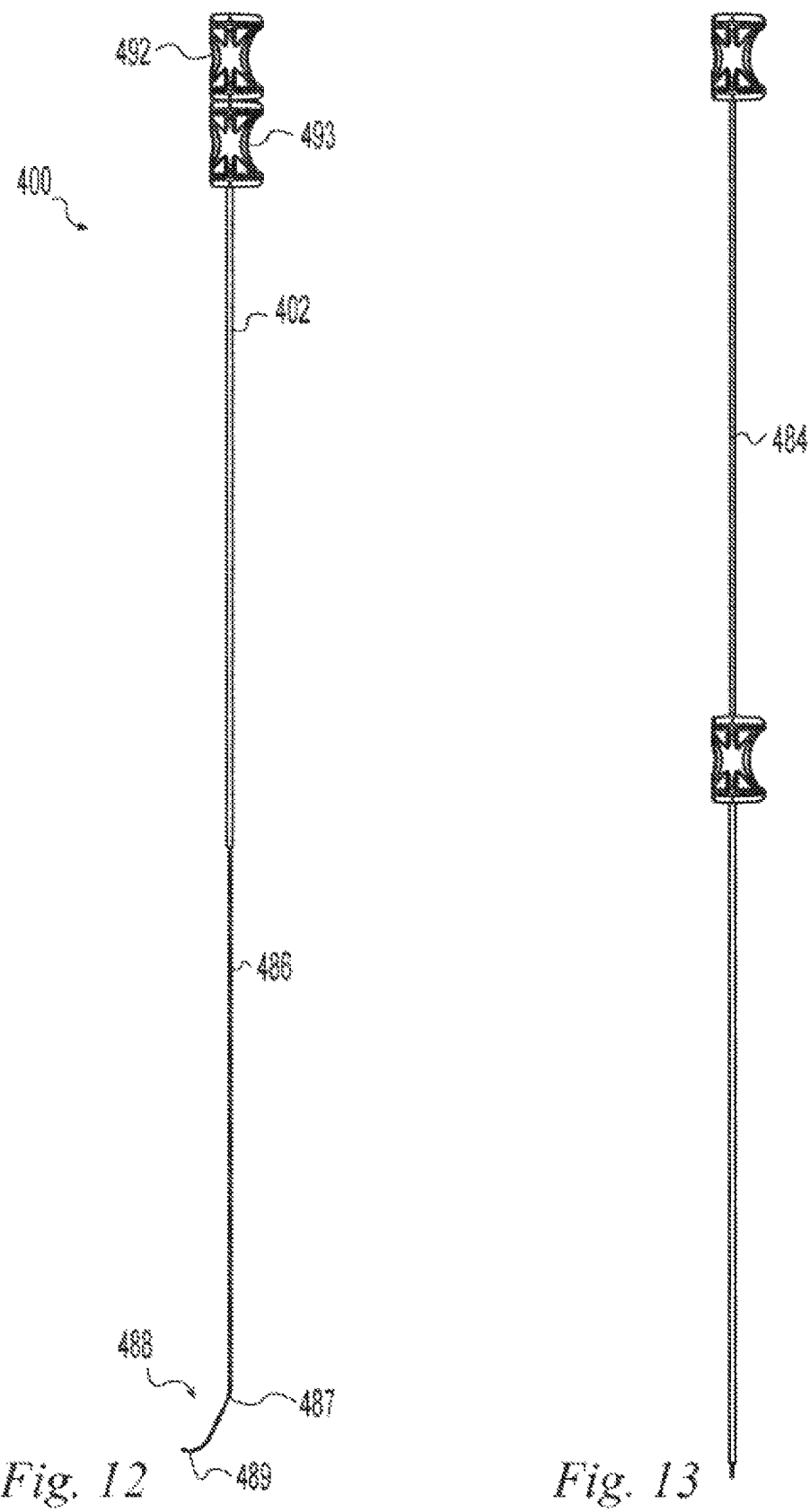

TRANSOSSEOUS GUIDE AND METHOD

CROSS-REFERENCE TO RELATED APPLICATIONS

This application is a continuation-in-part of U.S. patent application Ser. No. 15/211,764, filed Jul. 15, 2016 and titled TRANSOSSEOUS GUIDE, which claims the benefit of U.S. Provisional Application No. 62/193,888, filed Jul. 17, 2015 and titled TRANSOSSEOUS GUIDE AND METHOD. This application is also a continuation-in-part of U.S. patent application Ser. No. 15/211,673, filed Jul. 15, 2016 and titled TRANSOSSEOUS METHOD, which also claims the benefit of U.S. Provisional Application No. 62/193,888. Each of the above named applications is incorporated by reference, as if set forth herein in its entirety.

TECHNICAL FIELD

The present disclosure relates to transosseous guides and methods for transosseous attachments.

BACKGROUND

A variety of surgical procedures require the attachment of something relative to a surgical site. For example, in surgery relating to the skeletal system, it is often advantageous to attach soft tissue, suture, implants, and/or other items in or adjacent to a joint. For example, soft tissues such as ligaments, tendons, fascia, other capsular material, and/or muscle may be attached to an adjacent bone. Such soft tissues may be adjacent to bones at skeletal joints including but not limited to the joints of the hands and feet, ankle, wrist, knee, elbow, hip, shoulder, and spine. For example, it is often advantageous to pass a suture through a portion of a bone to form a transosseous attachment to the bone.

SUMMARY

Examples of the present disclosure provide instruments and methods for surgical transosseous attachment to a bone.

In one example of the present disclosure, a system for placing a flexible member transosseously through first and second transverse, intersecting bone tunnels may include a guide body having a guide body handle portion and a longitudinal guide body passage. The system may also include a first tunnel member engaged with the guide body that includes a proximal end, a distal end, a first longitudinal passage extending through the first tunnel member, at least one curved portion nearer the distal end of the first tunnel member than the proximal end of the first tunnel member, and a first guide axis associated with the distal end of the first tunnel member, where at least a portion of the first longitudinal passage near the distal end of the first tunnel member is coaxial with the first guide axis. The system may also include a second tunnel member engaged with the longitudinal guide body passage that includes a proximal end, a distal end, and a second longitudinal passage extending at least partway through the second tunnel member. The second longitudinal passage may be coaxial with a second guide axis defined by the longitudinal guide body passage when the second tunnel member is engaged with the longitudinal guide body passage and at least a portion of the first longitudinal passage near the proximal end of the first tunnel member may be parallel to the second guide axis. The system may also include a passer operable to extend from the proximal end of the first tunnel member, through the distal end of the first tunnel member, through the distal end of the second tunnel member, and to the proximal end of the second tunnel member in one continuous path.

In another example of the present disclosure, a system for placing a member transosseously through first and second bone tunnels may include a guide body with a longitudinal guide body passage. The system may also include a first tunnel member engaged with the guide body that has a proximal end, a distal end, and a first longitudinal passage extending through the first tunnel member. The system may also include a second tunnel member engaged with the longitudinal guide body passage that has a proximal end, a distal end, and a second longitudinal passage extending at least partway through the second tunnel member. The system may also include a passer operable to extend from the proximal end of the first tunnel member, through the distal end of the first tunnel member, through the distal end of the second tunnel member, and to the proximal end of the second tunnel member in one continuous path.

In another example of the present disclosure, a method for placing a member transosseously through first and second transverse, intersecting bone tunnels that includes inserting a first tunnel member into a bone along a first insertion axis, the first tunnel member having a proximal end, a distal end, and a first longitudinal passage extending through the first tunnel member. The method may also include inserting a second tunnel member into the bone along a second insertion axis that intersects the first insertion axis, the second tunnel including a proximal end, a distal end, and a second longitudinal passage extending at least partway through the second tunnel member. The method may also include inserting a passer through the first and second tunnel members in one continuous motion until the passer extends through the first longitudinal passage, the second longitudinal passage, out of the proximal end of the first tunnel member, and out of the proximal end of the second tunnel member.

BRIEF DESCRIPTION OF THE DRAWINGS

Various examples of the present disclosure will be discussed with reference to the appended drawings. These drawings depict only illustrative examples of the present disclosure and are not to be considered limiting of its scope.

FIG. 12 is a side elevation view of an example of the present disclosure illustrating an alternative arrangement of the passer of FIG. 2 in a first position;

FIG. 13 is a side elevation view of the example of FIG. 12 in a second position;

DETAILED DESCRIPTION

Figure 1:
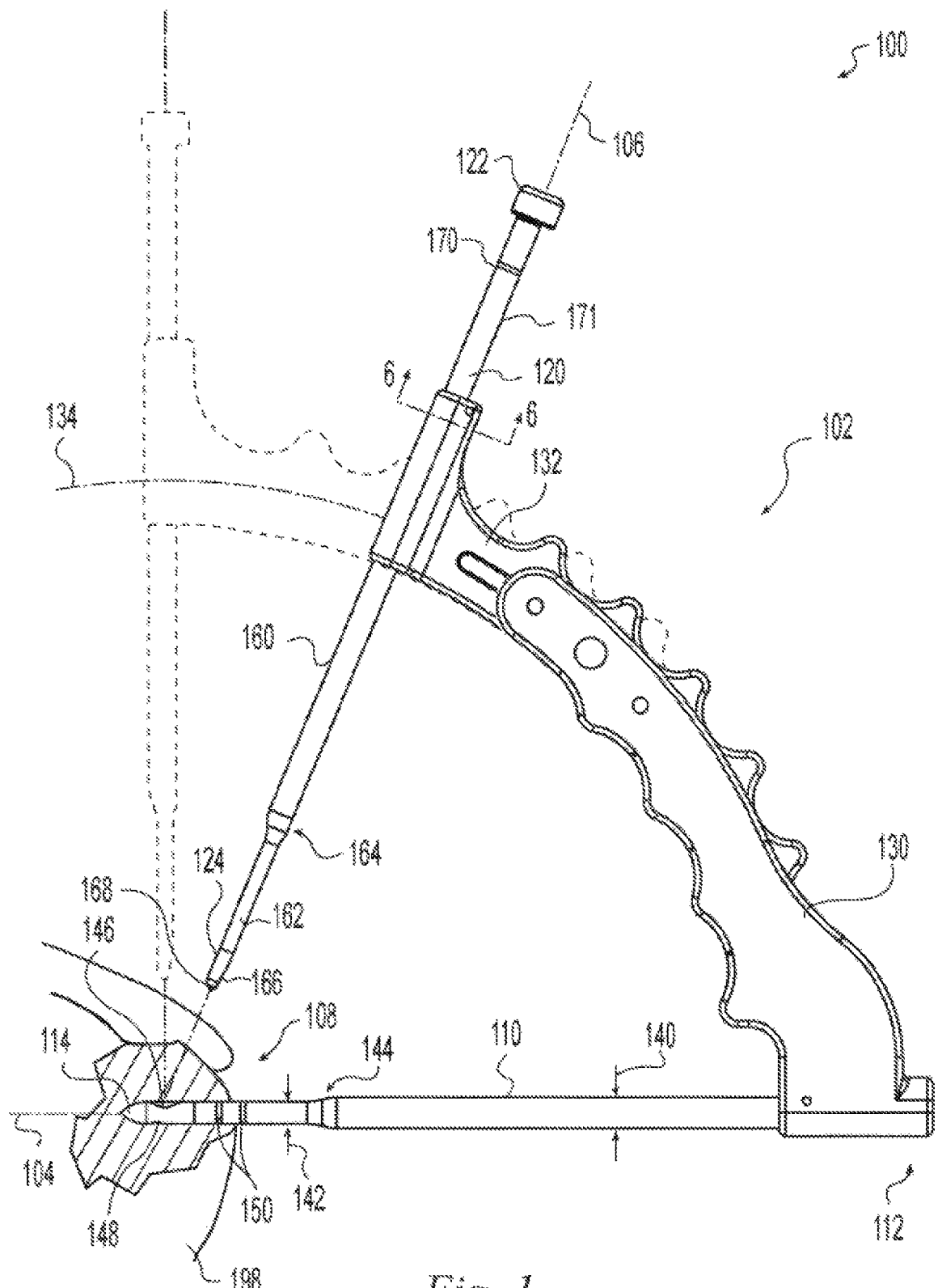
FIG. 1 is a side elevation view of an example of the present disclosure illustrating an instrument engaged with a bone, the bone being shown in partial section.

The following illustrative examples depict instruments and methods to form a tunnel through a bone and pass a member through the bone tunnel. The illustrative examples depict passing a round suture through a bone tunnel to attach soft tissue to the bone. However, the instruments and methods of the present disclosure may be used to pass other elements through a bone tunnel including, suture passers, suture tapes, cables, soft tissues, grafts, and other elements. Examples of instruments and methods of the present disclosure may be used to pass any member through any bone, at surgical sites anywhere in a patient's body, and for any purpose. The terms "suture" and "suture strand" are used herein to mean any strand or flexible member, natural or synthetic, able to be passed through a bone tunnel and useful in a surgical procedure. The term "transverse" is used herein to mean to cross at an angle; i.e. not parallel. The term includes, but is not limited to right angles.

FIGS. 1-8 depict examples of a guide and a passer for forming intersecting bone tunnels in a bone 198 and passing a flexible element through the tunnels. The exemplary guide 100 includes a guide body 102 defining a first insertion or guide axis 104 and a second insertion or guide axis 106 intersecting at a location 108 spaced from the guide body.

A first tunnel member 110 is engageable with the guide body 102 coaxial with the first guide axis 104 and includes a proximal end 112, a distal end 114, and a first longitudinal passage 116 (FIG. 7) at least partway through the first tunnel member 110.

A second tunnel member 120 is engageable with the guide body 102 coaxial with the second guide axis 106 and includes a proximal end 122, a distal end 124, and a second longitudinal passage 126 (FIG. 7) at least partway through the second tunnel member 120.

A passer 136 (FIG. 2) is operable to extend from the proximal end 122 of the second tunnel member 120, through the distal end 124 of the second tunnel member 120, through the distal end 114 of the first tunnel member 110, and to the proximal end 112 of the first tunnel member 110 in one continuous path. The passer 136 may then be used to pull a flexible member or element such as, for example, a passing suture or a repair suture through the tunnel members 110, 120 to pass the flexible element through, for example, a bone.

In the illustrative embodiment of FIGS. 1-8, the guide body 102 is made up of first and second arc members 130, 132. The first and second arc members 130, 132 are joined in sliding relationship along an arc shaped path 134 of constant radius such that the guide 100 is adjustable between a first position (shown in solid lines in FIG. 1) in which the first guide axis and the second guide axis define a first angle between them and a second position (shown in dashed lines in FIG. 1) in which the first guide axis and the second guide axis define a second, larger angle between them. Preferably, the guide is continuously adjustable over a range of included angles between the first and second guide axes 104, 106 of from 20 to 110 degrees. More preferably, the range is 60 to 90 degrees. In the illustrative example of FIGS. 1-8, the first guide axis 104 is defined by a passage in the first arc member 130 and the second guide axis 106 is defined by a passage in the second arc member 132.

The first tunnel member may include a drill guide, a punch guide, a punch, or other suitable member for forming a bone tunnel and/or for inserting into a bone tunnel. In the illustrative example of FIGS. 1-8, the first tunnel member 110 is a bone punch fixed to the guide body such as by pinning, threading, welding, or other suitable fixation method. For example, the first tunnel member 110 may be impacted into the bone 198 to form a bone tunnel in the bone. In the illustrative example of FIGS. 1-8, the first tunnel member 110 includes a cylindrical body having a first, larger diameter 140 near its proximal end 112 and a second, smaller diameter 142 near its distal end with a tapered transition region 144 between the two diameters. The cylindrical body defines a first outer side wall and a first recess or side opening 146 (FIG. 7) in the first side wall nearer the distal end 114 than the proximal end 112. The second guide axis 106 passes through the first side opening 146 for every angle in the range of adjustment of the first and second arc members 130, 132. The first longitudinal passage 116 extends from the proximal end 112 of the first tunnel member 110 toward the distal end 114 and communicates with the first side opening 146. A relief opening 148 in the side wall is positioned opposite the first side opening 146 and communicates with the first longitudinal passage 116 and the first side opening 146. The first tunnel member 110 includes indicia 150 (FIG. 1) on the outer surface readable relative to the bone surface to indicate a depth of penetration of the first tunnel member 110 into the bone. In the illustrative example of FIGS. 1-8, the indicia 150 include two separate marks to indicate the appropriate depth for two different sizes of anchor. In the illustrative example of FIGS. 1-8, the first tunnel member 110 tapers to a solid, sharp point 152 distal to the first side opening 146 and the relief opening to facilitate driving the first tunnel member 110 into bone.

The second tunnel member may include a drill guide, a punch guide, a punch, or other suitable member for forming a bone tunnel and/or inserting into a bone tunnel. In the illustrative example of FIGS. 1-8, the second tunnel member 120 is a punch engageable with the guide 100 in axial sliding relationship along the second guide axis 106. For example, the second tunnel member 120 may be impacted into the bone 198 to form a bone tunnel in the bone. In the illustrative example of FIGS. 1-8, the second tunnel member 120 includes a body having a "D"-shaped proximal portion 160 and a smaller cylindrical distal portion 162 with a tapered transition region 164 between the two portions. The body defines a second outer side wall and a second side opening 166 (FIG. 7) in the first side wall nearer the distal end 124 than the proximal end 122. In the illustrative example of FIGS. 1-8, the second longitudinal passage 126 extends from the proximal end 122 of the second tunnel member 120 toward the distal end 124 of the second tunnel member 120 and communicates with the second side opening 166. The second tunnel member 120 tapers to a solid, sharp point 168 distal to the second side opening 166 to facilitate driving the second tunnel member 120 into bone. The second tunnel member 120 includes an indicator to indicate when it is engaged with the first tunnel member 110. In one example, the second tunnel member 120 includes an index mark 170 on the outer surface readable relative to the guide 100 to indicate a depth of penetration of the second tunnel member 120 into the bone. In the illustrative example of FIGS. 1-8, the distal portion 162 of the second tunnel member 120 is engageable within the first side opening 146 of the first tunnel member with the first side opening 146 and second side opening 166 in communication with one another. The index mark 170 on the second tunnel member 120 indicates when the distal end of the second tunnel member 120 is seated in the first side opening 146. In another example, the second tunnel member 120 has an elongated marker such as for example a contrasting surface 171 that is exposed to indicate when the second tunnel member is not properly seated. The surface 171 extends proximally-distally the distance of the engagement of the second tunnel member 120 with the guide body 102. When the second tunnel member 120 is properly seated, the surface 171 is covered by the guide body 102. If the second tunnel member 120 is not fully seated, the surface 171 is visible above the guide body. If the second tunnel member is inserted too far, for example if it deflects upon insertion such that it misses the first tunnel member and is driven past the first tunnel member, the surface 171 is visible below the guide body. In one example, the surface 171 includes a colored stripe, for example a red colored stripe, such that if red is visible after inserting the second tunnel member it indicates that the second tunnel member is not properly seated. For example, in FIGS. 1 and 21 the surface 171 is visible above the guide body 102 and in FIGS. 5 and 22 the surface 171 is concealed by the guide body 100.

The relief opening 148 in the first tunnel member allows bone chips or other debris to exit the first tunnel member 110 when the second tunnel member 120 engages it. In the illustrative example of FIGS. 1-8, an angled surface 172 is formed at the distal end of the second longitudinal passage 126 facing the second side opening 166. The angled surface 172 deflects the passer 136 through the second side opening 166 and into the first longitudinal passage 116 when the passer is inserted. The "D"-shape of the proximal portion 160 of the second tunnel member 120 engages the guide 100 to prevent rotation of the second tunnel member 120 as it axially translates so that the first and second side openings 146, 166 are aligned when the first and second tunnel members 110, 120 are engaged.

The length of the first and second tunnel members 110, 120 that extends from the guide body to their intersection location may be any desired length. However, it has been found by the inventors that for rotator cuff repair surgery on a human shoulder, a length of each member in the range of 2-8 inches is useful. More preferably the length is in the range of 4-6 inches. The length for each member may be the same or different. In the example of FIGS. 1-8, the length of the first tunnel member extending from the guide body is approximately 5.5 inches and the length of the second tunnel member extending from the guide body is approximately 4.5 inches.

Figures 5, 6:
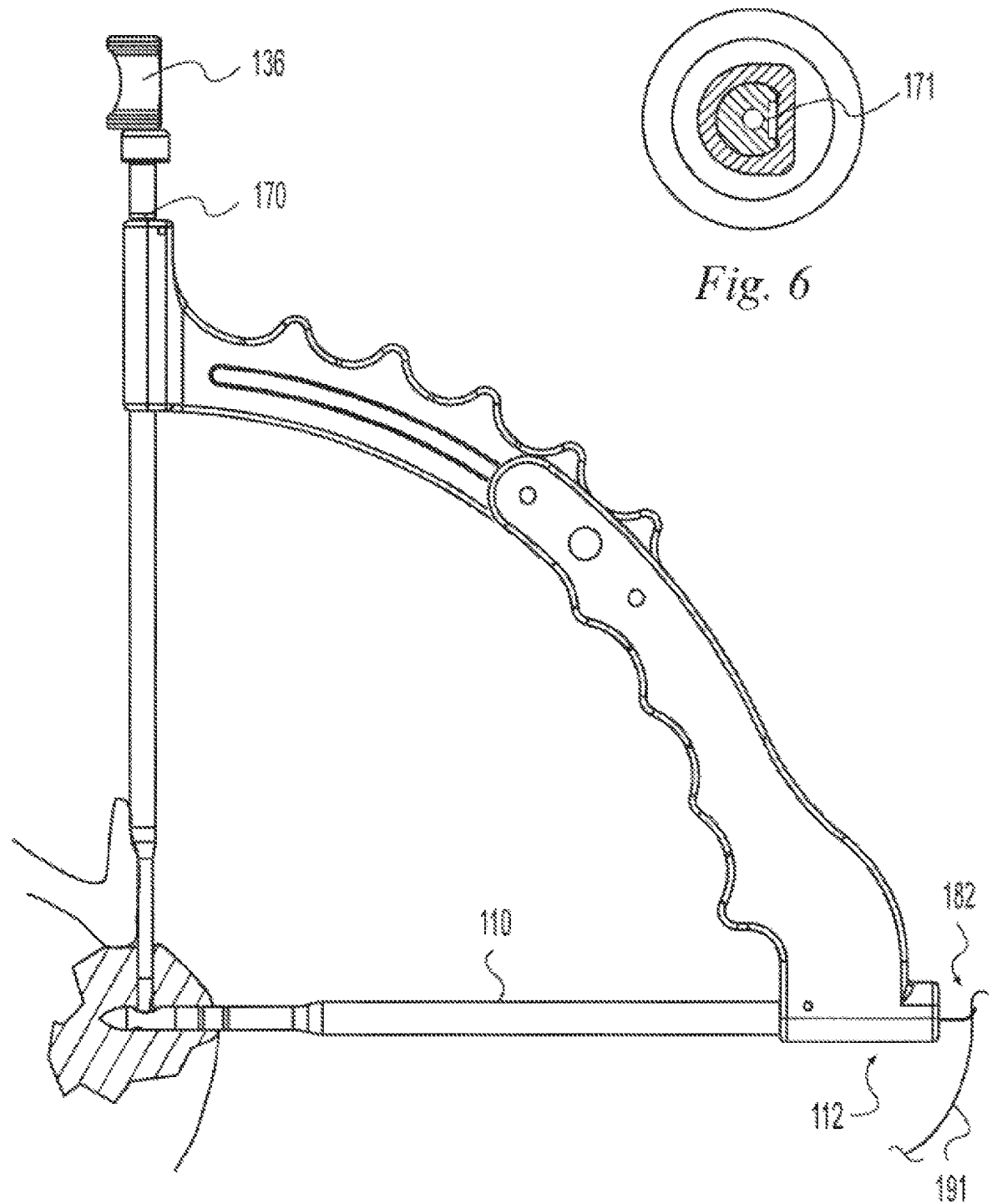
FIG. 5 is a side elevation view of the instrument of FIG. 1 engaged with a bone and the passer of FIG. 2 inserted through the instrument.
FIG. 6 is a section view taken along line 6-6 of FIG. 1.
Figure 7:
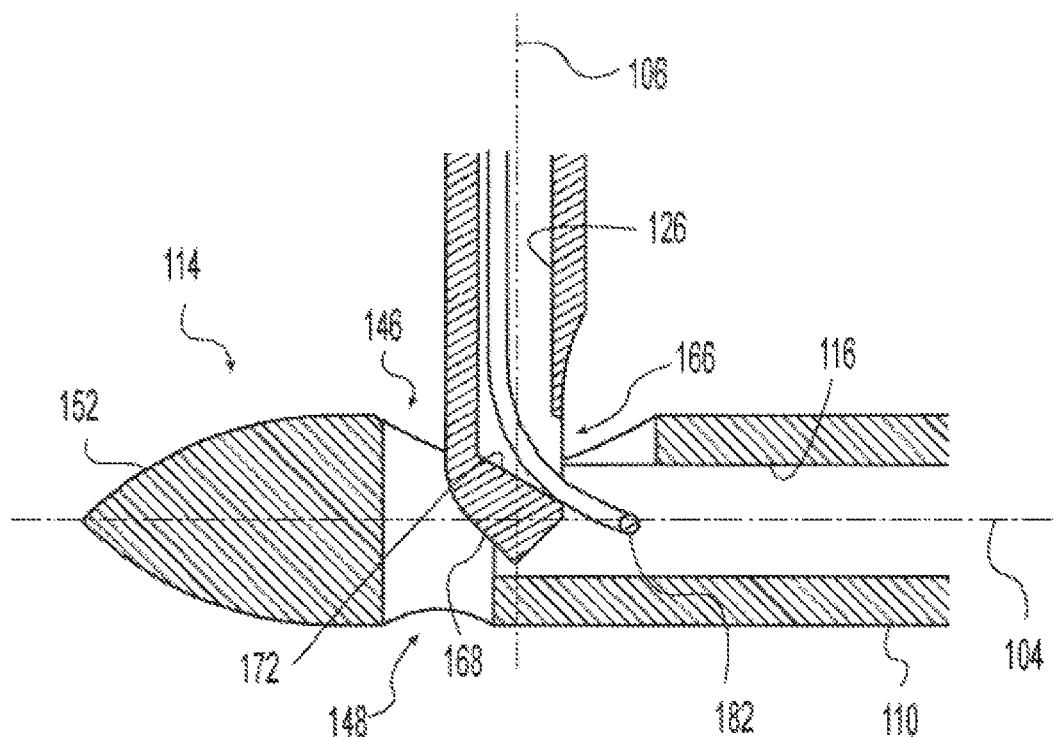
FIG. 7 is detail side section view of the instrument of FIG. 1 showing the passer engaged with the instrument in a first position.
Figure 8:
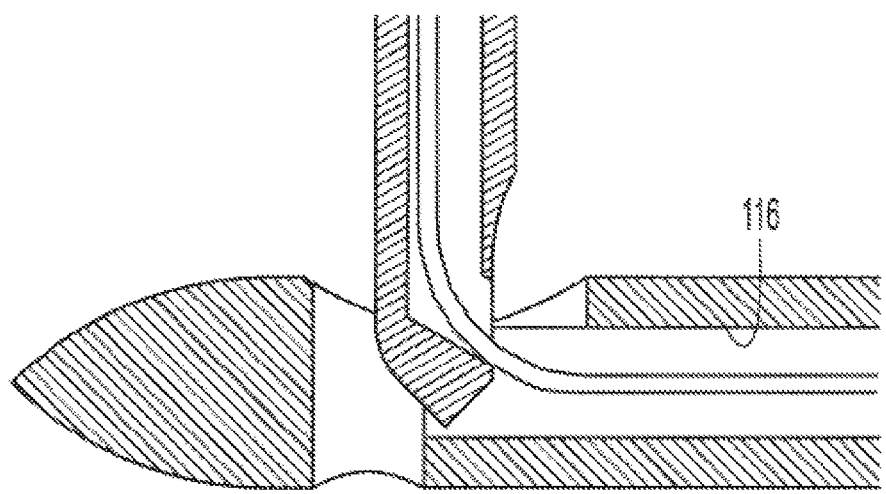
FIG. 8 is detail side section view of the instrument of FIG. 1 showing the passer engaged with the instrument in a second position.

The passer 136 includes a first, or proximal, end 180 and a second, or distal, end 182 defining a loop 188. In the illustrative example of FIGS. 1-8, the passer 136 includes a relatively rigid shaft 184 extending away from the first end and a relatively flexible wire 186 attached to the shaft 184 and extending away from the shaft 184. In one example, the shaft 184 is a tubular member and the wire 186 is crimped, bonded, soldered, welded or otherwise attached to the shaft. In the illustrative example of FIGS. 1-8, the wire 186 is formed into a loop 188 in a first plane and bent to form a curved profile 190 in a second plane perpendicular to the first plane. The curved profile 190 of the wire and the angled surface 172 at the distal end of the second longitudinal passage 126 cooperate to facilitate advancing the distal end 182 of the passer from the second longitudinal passage 126 into the first longitudinal passage 116. The passer 136 includes a handle 192 at the proximal end 180. Preferably, the passer, or at least the wire 186, is formed of a super elastic material such as nitinol, as one non-limiting example. Preferably the combined length of the shaft 184 and wire 186 is greater than the combined length of the first and second longitudinal passages 116, 126 such that the passer 136 is insertable through the first and second tunnel members 110, 120 to extend through the first and second axial passages and out of the proximal end 112 of the first tunnel member 110 and out of the proximal end 122 of the second tunnel member 120. For example, as the distal end 182 of the passer reaches the distal end of the second longitudinal passage 126, it abuts the angled surface 172 and is deflected out through the second side opening 166, through the first side opening 146 and into the first longitudinal passage 116 (FIG. 7). The curved profile 190 of the wire and angled surface 172 facilitate the transition of the wire 186 from the second tunnel member 120 to the first tunnel member 110 and promote passage even when the first and second tunnel members 110, 120 are engaged at an acute angle. The passer is further advanced to move the distal end 182 of the passer through the second longitudinal passage and out the proximal end 112 of the first tunnel member 110 (FIG. 5). A member 191, e.g. a suture, may be placed in the loop 188 at the distal end 182 of the passer and the passer 136 may be retrieved to pull the member 191 through the first longitudinal passage 116, through the first side opening 146, through the second side opening 166, through the second longitudinal passage 126 and out the proximal end of the second longitudinal passage 126. The passer handle includes an indicator, for example a flat surface 197, to indicate to a user the orientation of the bent loop 188 so that the user can orient it to engage the angled surface 172. Alternatively, or in addition, the passer may be keyed to the second tunnel member to permit only one orientation.

Figure 9:
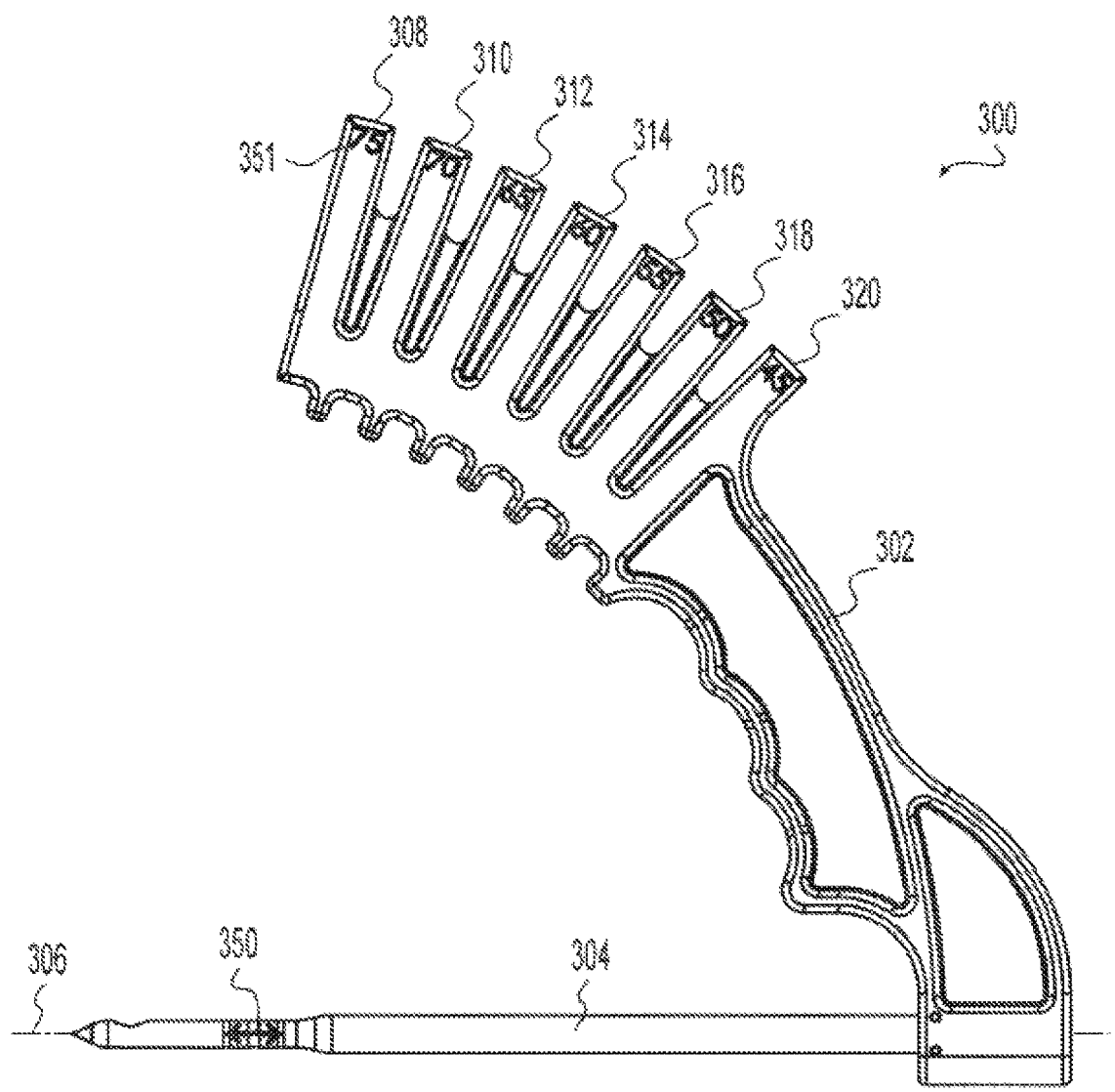
FIG. 9 is a side elevation view of an example of the present disclosure illustrating an alternative arrangement of the instrument of FIG. 1.
Figure 10:
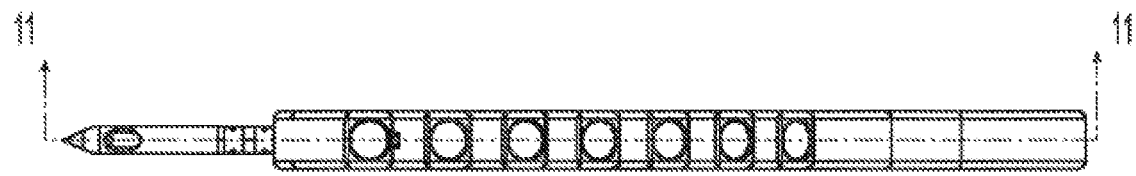
FIG. 10 is a top plan view of the instrument of FIG. 9.
Figure 11:
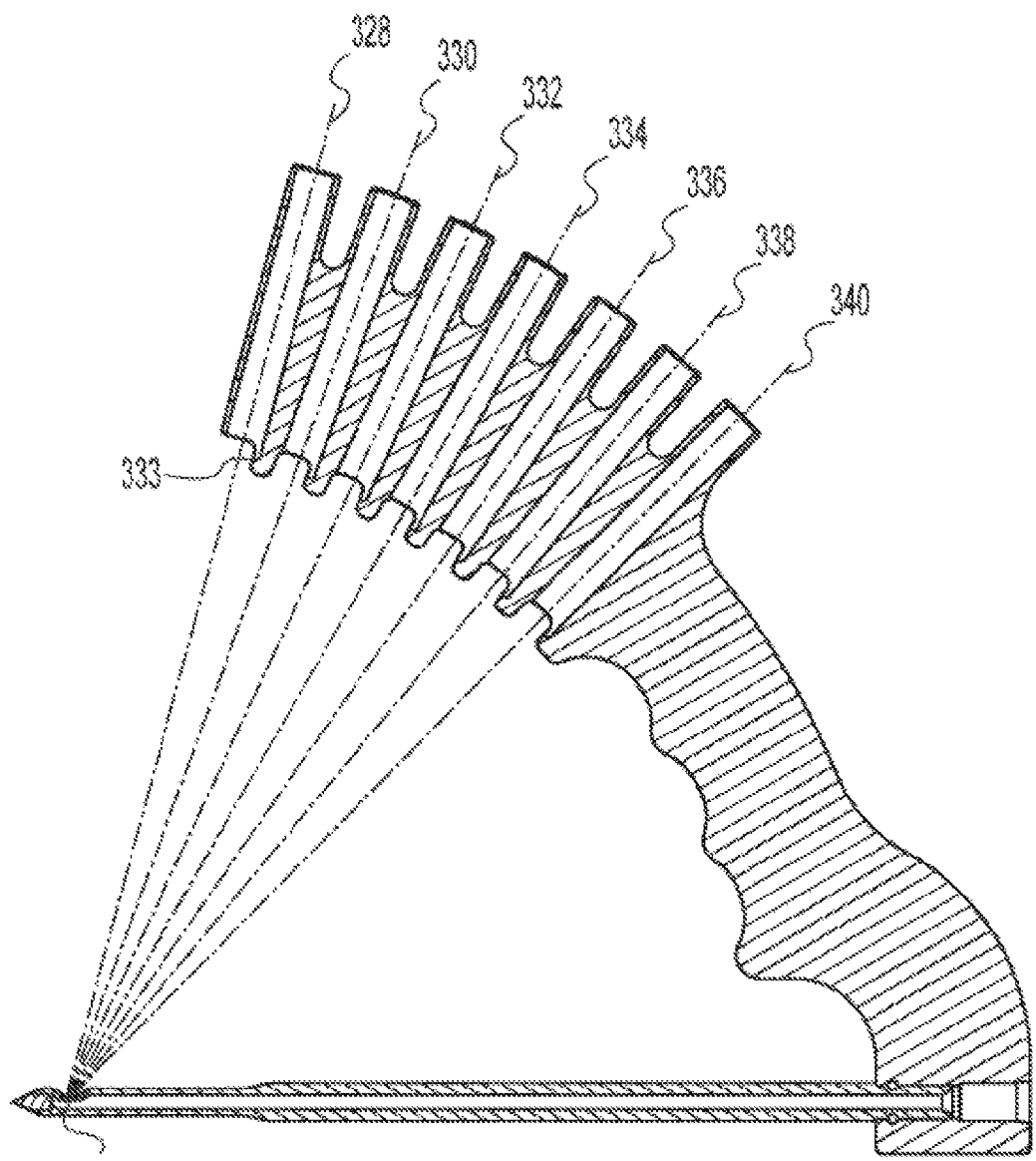
FIG. 11 is a section view taken along line 11-11 of FIG. 10.

FIGS. 9-11 illustrate another example of a guide instrument 300 similar to that of FIG. 1 but showing a different arrangement of the second guide axis. The guide body 302 includes a first tunnel member 304 like the first tunnel member in the example of FIG. 1 that defines a first guide axis 306 as with the example of FIG. 1. However, the guide body is a unitary body having a plurality of receivers 308, 310, 312, 314, 316, 318, 320 operable to receive the second tunnel member 120. Each receiver includes a passage defining a guide axis. Any number of receivers may be included at any desired spacing to provide a desired selection of guide angles relative to the first guide axis. In the example of FIGS. 9-11, seven receivers are provided defining a second guide axis 328, a third guide axis 330, a fourth guide axis 332, a fifth guide axis 334, a sixth guide axis 336, a seventh guide axis 338, and an eighth guide axis 340. Each of the second through eighth guide axes intersects the first guide axis 304 at the same location spaced from the guide body and each can selectively receive the second tunnel member. In the example of FIGS. 9-11, each of the second through eighth guide axes intersects a side opening 346 in the first tunnel member like the side opening 146 in the example of FIG. 1. A surface 333 formed at the distal end of each receiver engages the flat side of the "D"-shaped second tunnel member 120 to prevent rotation of the second tunnel member 120 within the receiver so that the first and second side openings 146, 346 are properly aligned when the first and second tunnel members are engaged.

In the example of FIGS. 9-11, the second through eighth guide axes are equally spaced and define angles of 45 degrees to 75 degrees relative to the first guide axis 306. Indicia 350 on the first tunnel member 304 indicates an insertion depth range suitable for a fastener, for example a knotless fastener. Indicia 351 on each receiver indicates the angle corresponding to each receiver. The spacing can be any desired spacing and can be uniform or non-uniform to provide a range of angles useful to the user. The inventors have found the spacing and range shown in the example to be suitable for typical rotator cuff procedures of the human shoulder.

For other applications, such as for example for attaching soft tissue to a bone adjacent a knee joint, ankle, or other location, different spacing and angular range may be desirable. Similarly, the length of the first and second tunnel member may be varied. For example, for repairing a torn Achilles tendon, a guide having an angular range of 50 to 80 degrees has been found suitable with either a sliding adjustable guide like that of FIG. 1 or a unibody guide like that of FIG. 9. In a unibody guide, four receivers defining axes at 50, 60, 70 and 80 degrees relative to the first guide axis have been found to be suitable. Any length of first and second tunnel members may be used. However, for repairing a torn Achilles tendon, shorter lengths may advantageously be used. For example, first and second tunnel members each extending from the guide body a distance in the range of two to three inches has been found suitable.

Figure 2:
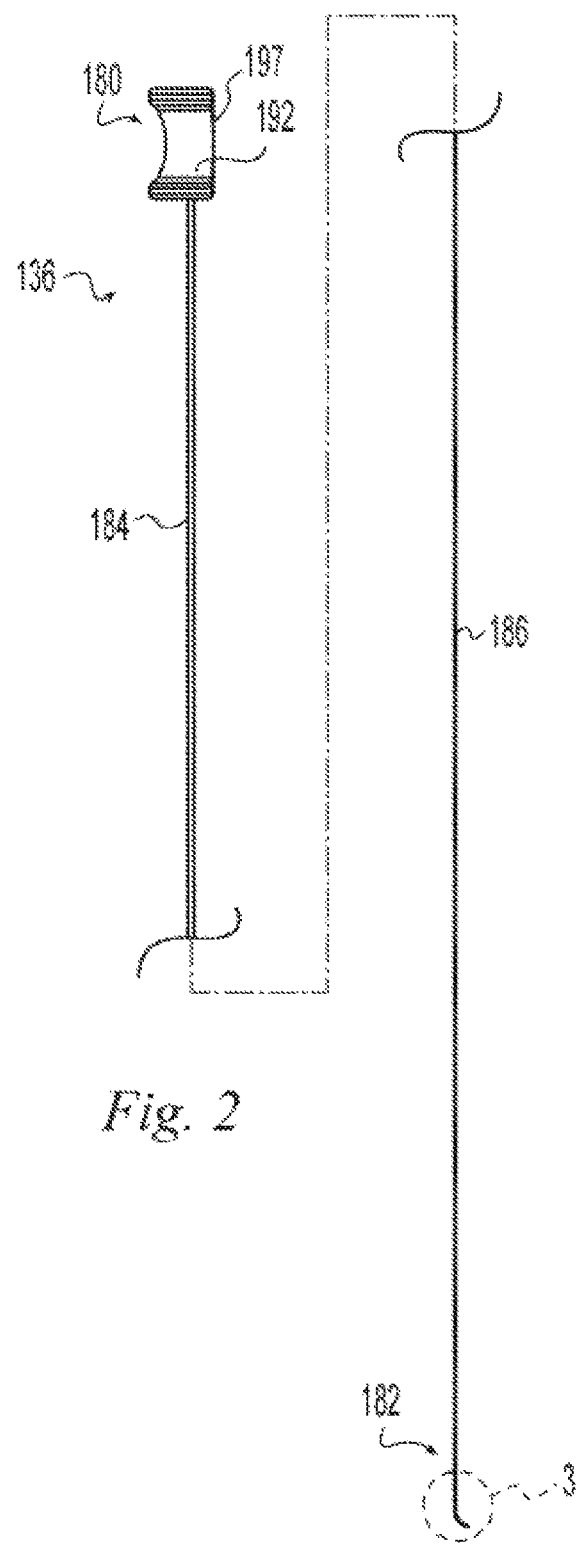
FIG. 2 is a side elevation view of an example of a passer used with the instrument of FIG. 1.
Figure 3:
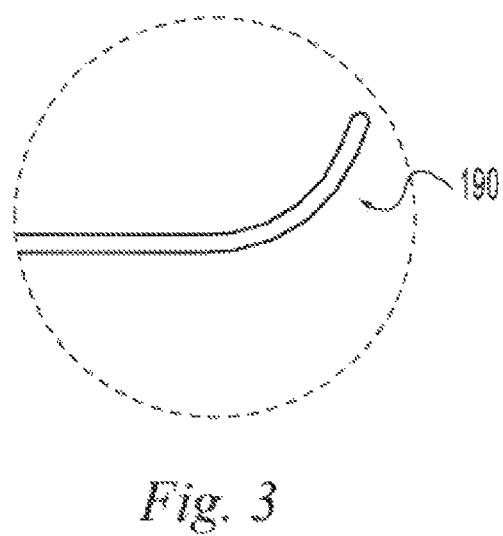
FIG. 3 is a detail side elevation view of the tip of the passer of FIG. 2.
Figure 4:
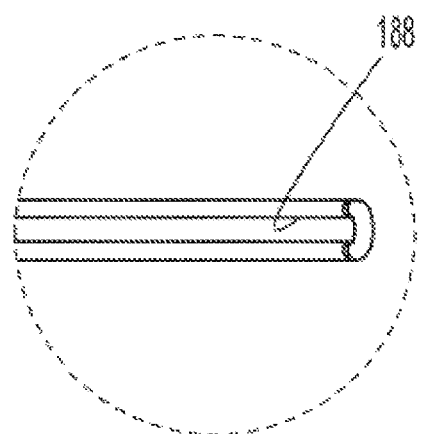
FIG. 4 is a detail front elevation view of the tip of the passer of FIG. 2.

FIGS. 12-13 illustrate another arrangement for a passer 400 similar to that of FIG. 2. The passer 400 includes an outer tube 402 engaged coaxially with the shaft 484 in axial sliding relationship and moveable relative to the shaft from a first position in which the outer tube encloses a portion of the wire length (FIG. 13) and a second position in which the outer tube encloses less of the wire length (FIG. 12). The outer tube is relatively rigid relative to the wire 486. The outer tube aids in inserting the passer 400 into the second tunnel member by holding the wire 486 in a straight and rigid configuration when the tube is in the first position. The outer tube may enclose any portion of the wire length in the first position to aid in inserting the passer. Preferably, in the first position, the outer tube encloses more than one-half of the wire length; more preferably 60 to 100 percent of the wire length; more preferably 80 to 100 percent of the wire length; more preferably the entire wire length including all of the loop 488. In the second position, enough of the wire is exposed to allow it to extend through the side openings in the first and second tunnel members and through the first tunnel member. Preferably in the second position, the outer tube encloses less than one-half of the wire length; more preferably less than 20 percent of the wire length. The tube may be inserted into the second tunnel member while in the first position and then shaft 484 advanced to extend the wire 486 out of the outer tube 402 and through the second and first tunnel members. For example, a handle 492 on the shaft may be pressed toward a handle 493 on the outer tube to advance the wire. The loop 488 in the example of FIGS. 12 and 13 includes a first bend 487 angled away from the main portion of the wire 486 and a second bend 489 at the distal end forming a small radius. The bends 487, 489 facilitate the transition of the loop through the side openings of the tunnel members.

Figure 14:
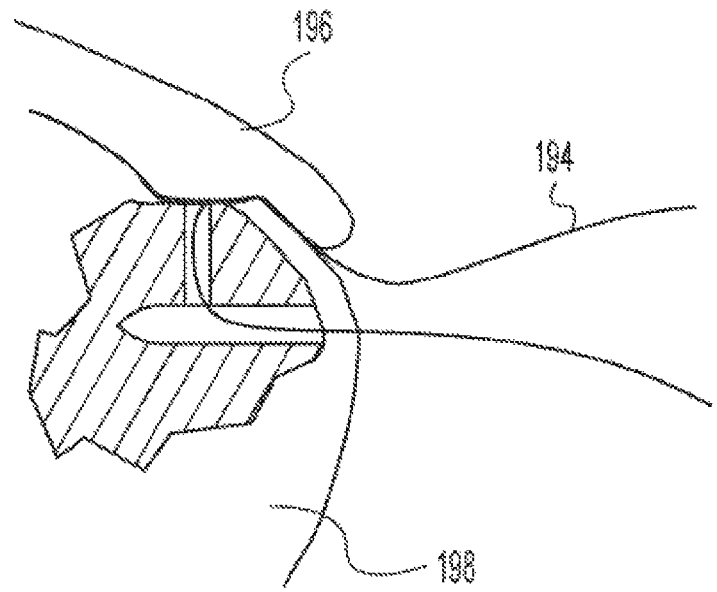
FIG. 14 is a partial sectional view of the bone of FIG. 1 after a suture has been passed and the passing instruments have been removed.
Figure 15:
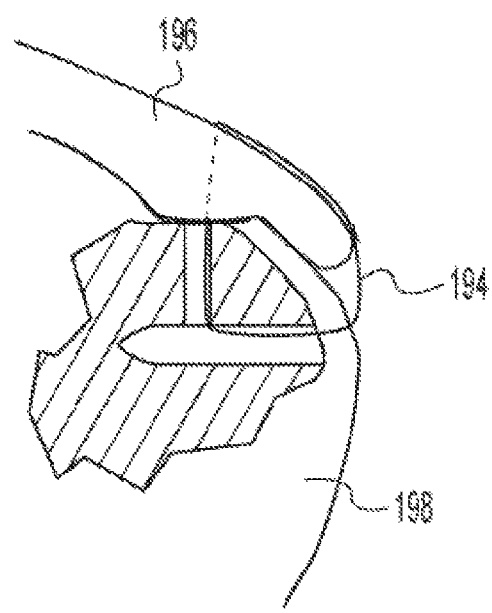
FIG. 15 is a partial sectional view illustrating the suture of FIG. 14 in use to secure a soft tissue to the bone.

The exemplary guides and methods of the present disclosure make it possible to form intersecting bone tunnels in a bone and extend, in one motion, a passer through the guide and bone tunnels from a first position external to the bone to a second position external to the bone. A first end of a member, such as a suture, may then be engaged with the passer outside of the bone tunnels. By having the engaging step outside of the bone tunnels, it may be done with simple manual manipulation of the passer loop and the first end of the member with easy access and visibility and without specialized arthroscopic instrument or procedures. The first end of the member may then be passed, in one motion, through the guide and bone tunnels from the second position external to the bone to a first position external to the bone to thread the member through the intersecting bone tunnels. The member may be used in any desirable manner. For example, a member in the form of a suture 194 may be so passed and then used to secure soft tissue 196 to the bone 198 as shown in FIGS. 14 and 15.

Figure 16:
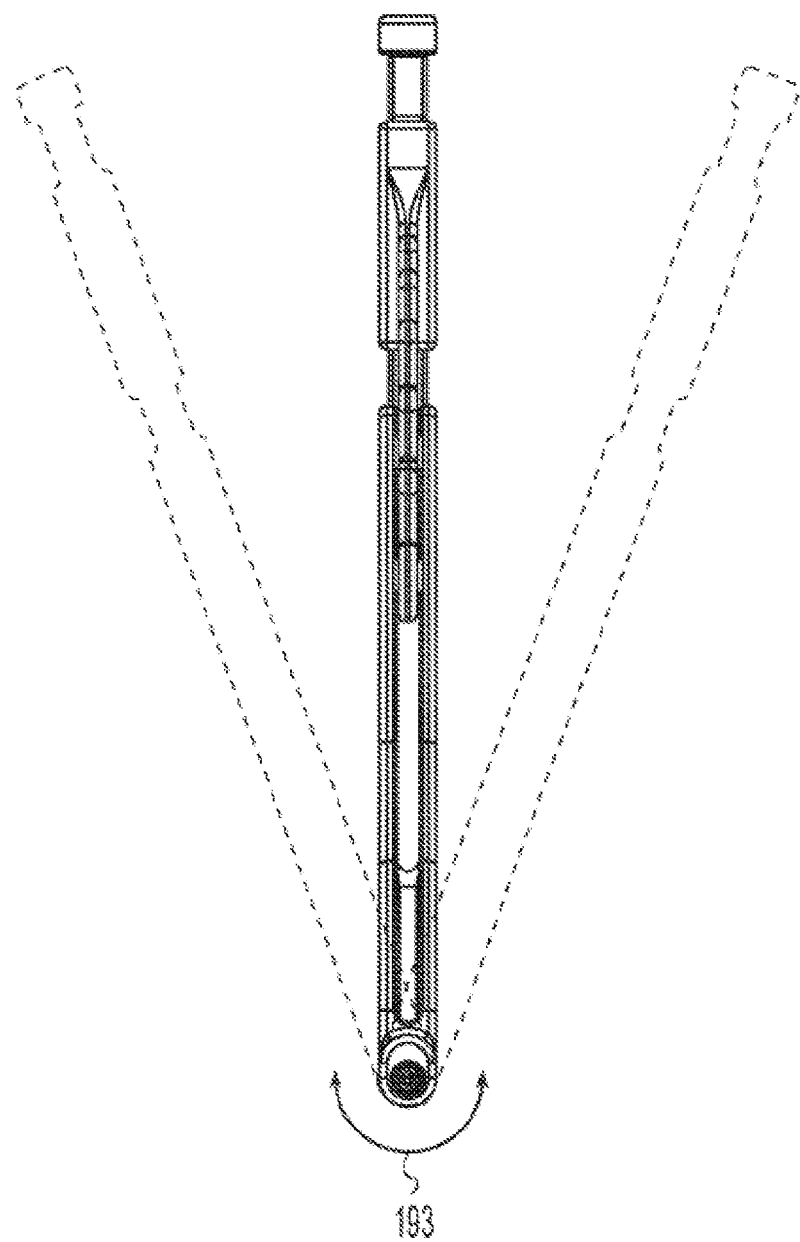
FIG. 16 is a rear elevation view of the guide of FIG. 1 illustrating how it can be rotated while engaged with a bone.
Figure 17:
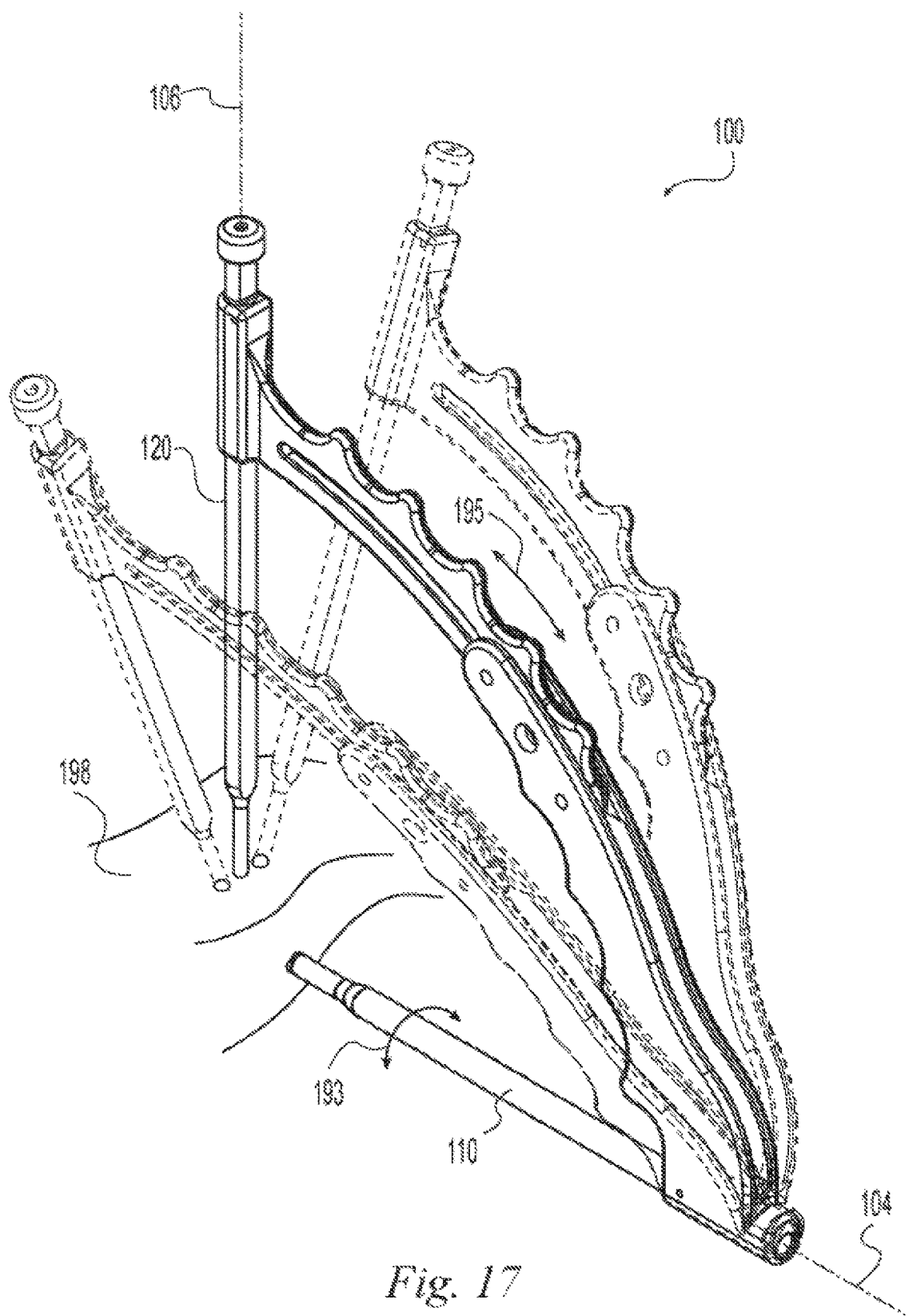
FIG. 17 is a perspective view of the guide of FIG. 1 illustrating how it can be rotated while engaged with a bone.

Referring to FIGS. 16 and 17, a guide according to examples of the present disclosure, for example guide 100 as shown in FIGS. 16 and 17, may be used to create three or more intersecting tunnels and pass flexible elements through the tunnels. For example, after passing a first flexible element through first and second intersecting tunnels in a bone 198, the second tunnel member 120 may be withdrawn from the bone. The guide 100 may be rotated about the first guide axis 104, as shown at reference numeral 193, and/or the angle between the guide axes 104 may be adjusted as shown at reference numeral 195 in FIG. 17. In a unitary guide such as the example of FIG. 9, the angle between the guide axes may be adjusted by inserting the second tunnel member in a different receiver. The second tunnel member 120 may then be inserted into the bone 198 in a new location and advanced to form a third bone tunnel intersecting the first bone tunnel. The second tunnel member 120 may be engaged with the first tunnel member 110 and the passer 136 used to pass a second flexible element through the first and third tunnels. This may be repeated as many times as desired to provide a one-to-many relationship between the first bone tunnel and the plurality of additional bone tunnels intersecting the first bone tunnel. The third and subsequent bone tunnels may be formed and the second and subsequent flexible elements may be passed while the first tunnel member 110 remains in the bone and while the first flexible element remains in the first tunnel member.

FIGS. 18-27 illustrate an example of a surgical method according to the present disclosure. In the illustrative example of FIGS. 18-27, instruments and methods of the previous examples are shown in use to place transosseous sutures to repair a rotator cuff 202 of a shoulder joint. It will be understood that any of the examples of instruments and methods of the present disclosure may be used in any combination to pass a member through a shoulder bone or other bones at a shoulder or other surgical sites and for rotator cuff repair or other surgical purposes.

Figure 18:
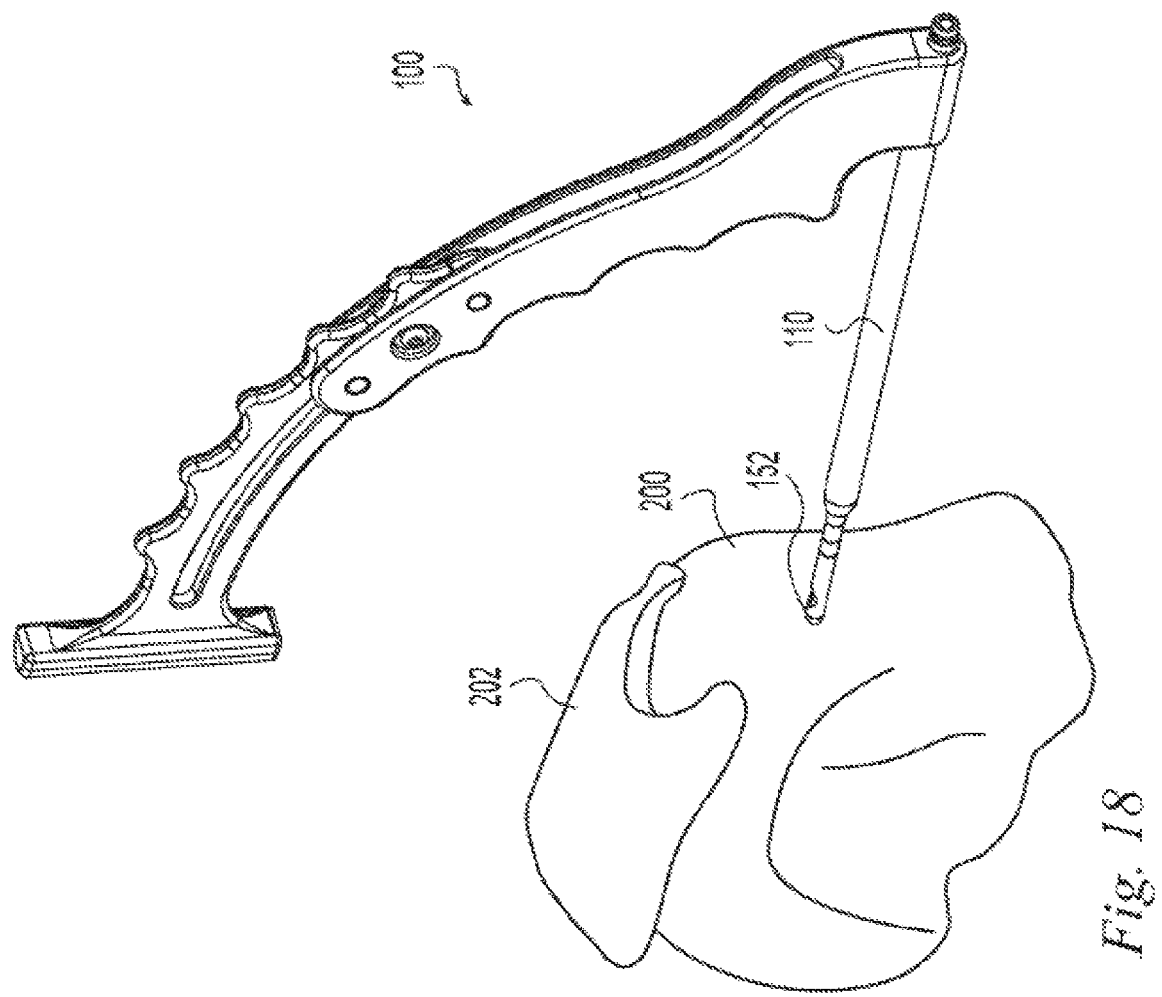
FIGS. 18-28 are perspective views of methods according to examples of the present disclosure.

Referring to FIG. 18 the guide 100 is positioned with the point 152 of the first tunnel member 110 on the lateral surface of the greater tuberosity 200 of the humerus approximately 30 mm inferior to the superior border of the tuberosity. The guide 100 is oriented such that it is perpendicular to the long axis of the humerus and perpendicular to the acromion (not shown).

Figure 19:
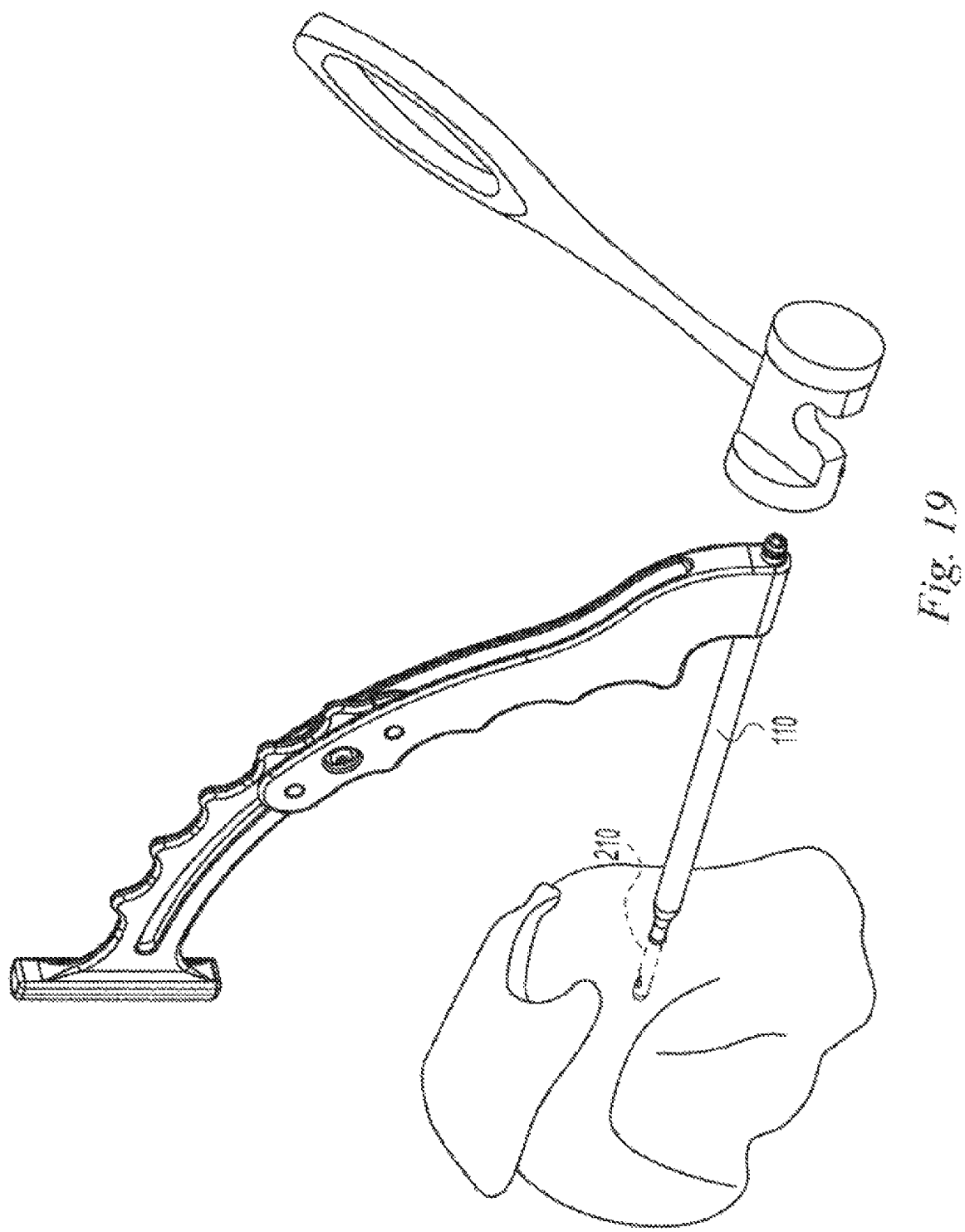

Referring to FIG. 19, the first tunnel member 110 is impacted into the bone to form a first, or lateral, bone tunnel 210.

Figure 20:
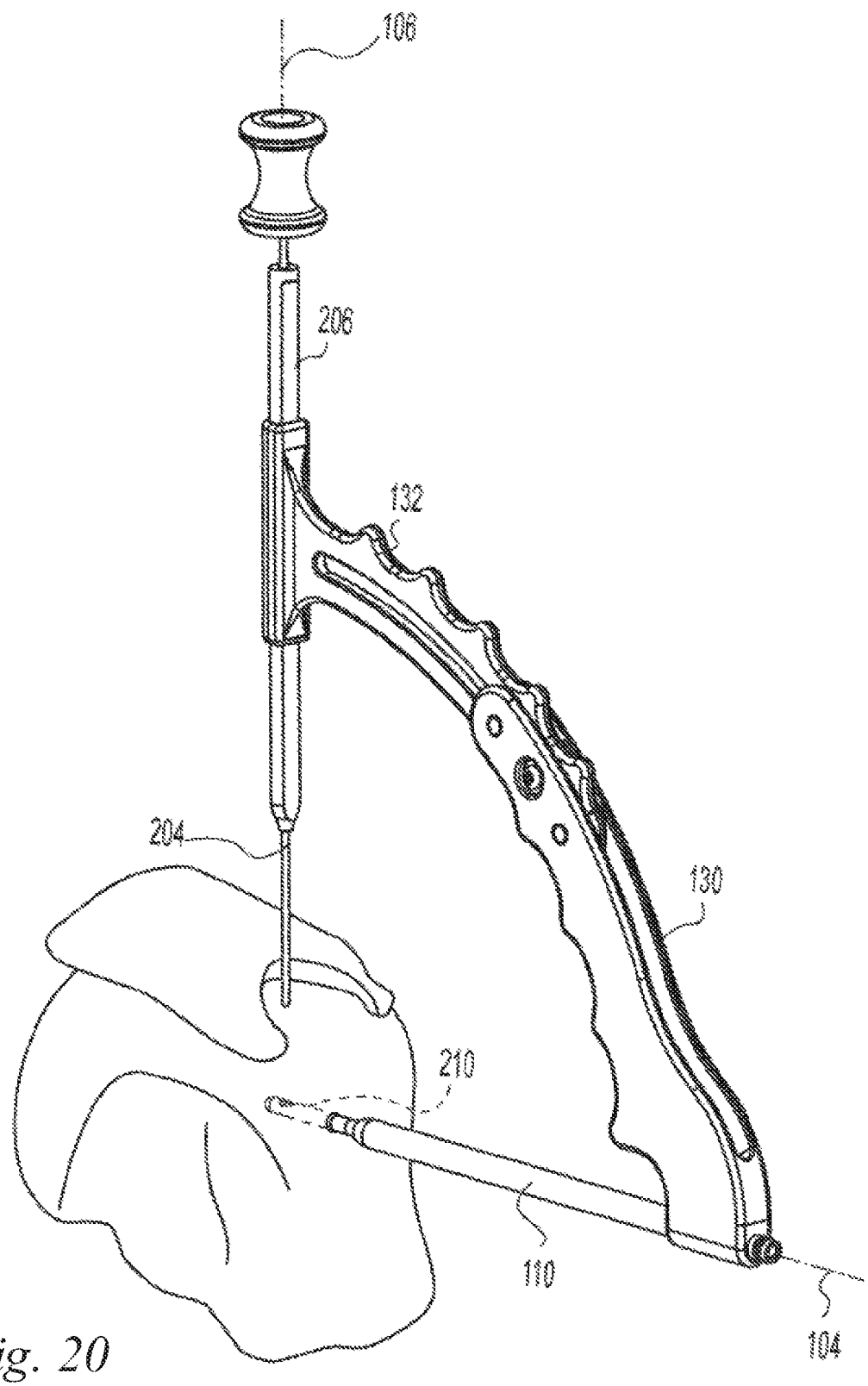

Referring to FIG. 20, the location for a second, or medial, tunnel is visualized using a targeting wire 204 in a targeting sleeve 206 to constrain the wire 204 to translation along the second guide axis 106. The position of the targeting wire may be adjusted in two degrees of freedom. First, the guide 100 may be rotated about the first guide axis 104 by twisting the first tunnel member 110 in the lateral bone tunnel 210. Second, the guide may be repositioned by adjusting the first and second arc members 130, 132 to change the angle between the guide axes 104, 106 (or repositioning the targeting sleeve and targeting wire in a different receiver in a unitary guide such as that of FIG. 9). As these adjustments are made, the targeting wire 204 may be inserted through the skin and other soft tissues near the targeted site so that the position may be visualized on the bone. The small punctures in the skin and other soft tissues created by the targeting wire 204 cause minimal trauma to the tissues and facilitate multiple targeting attempts if needed. The targeting wire 204 is then used to mark the bone surface with the desired medial tunnel location.

Figure 21:
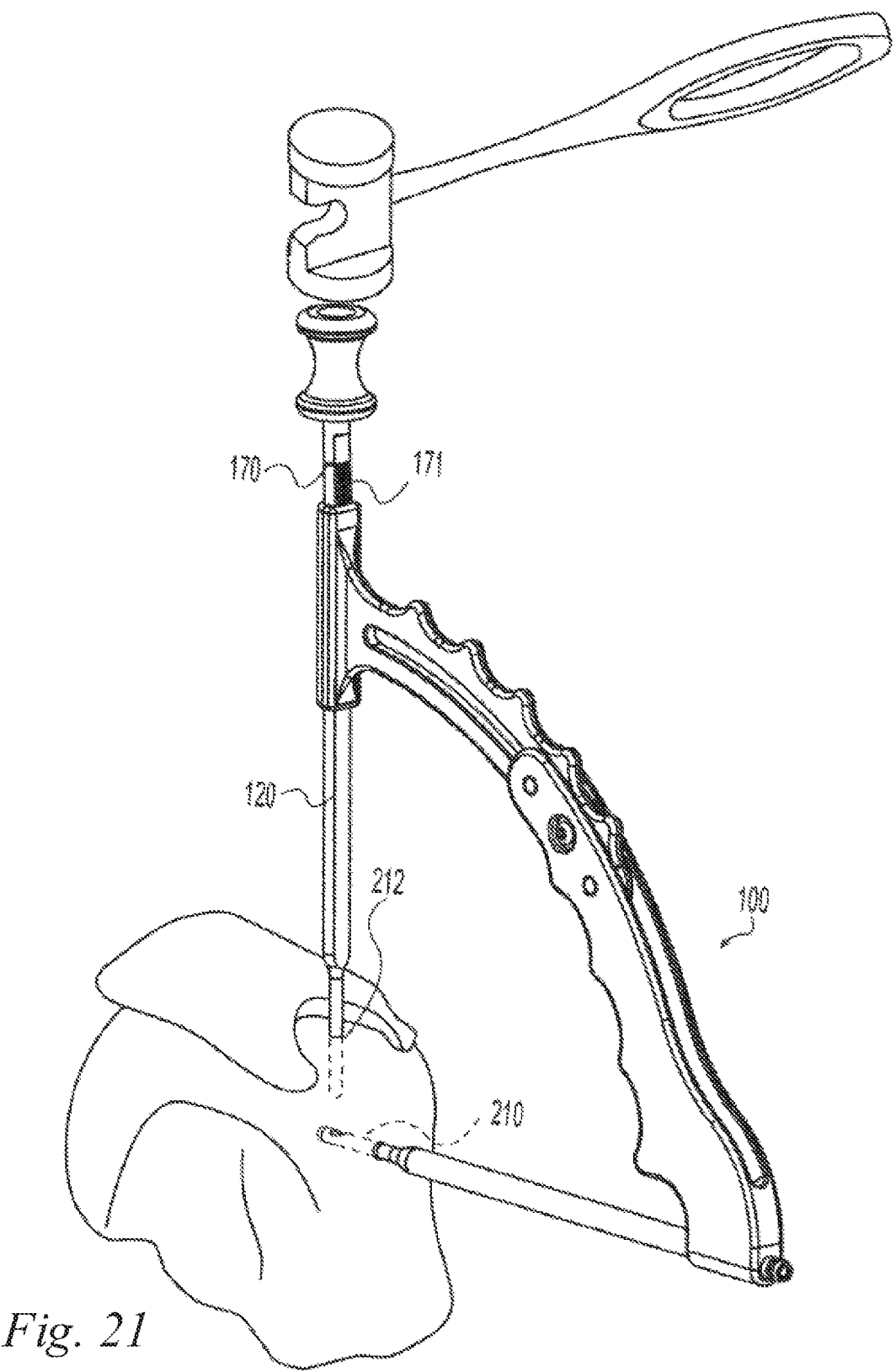

Referring to FIG. 21, the targeting sleeve and wire are removed and the second tunnel member 120 is impacted to form a second, or medial, tunnel 212.

Figure 22:
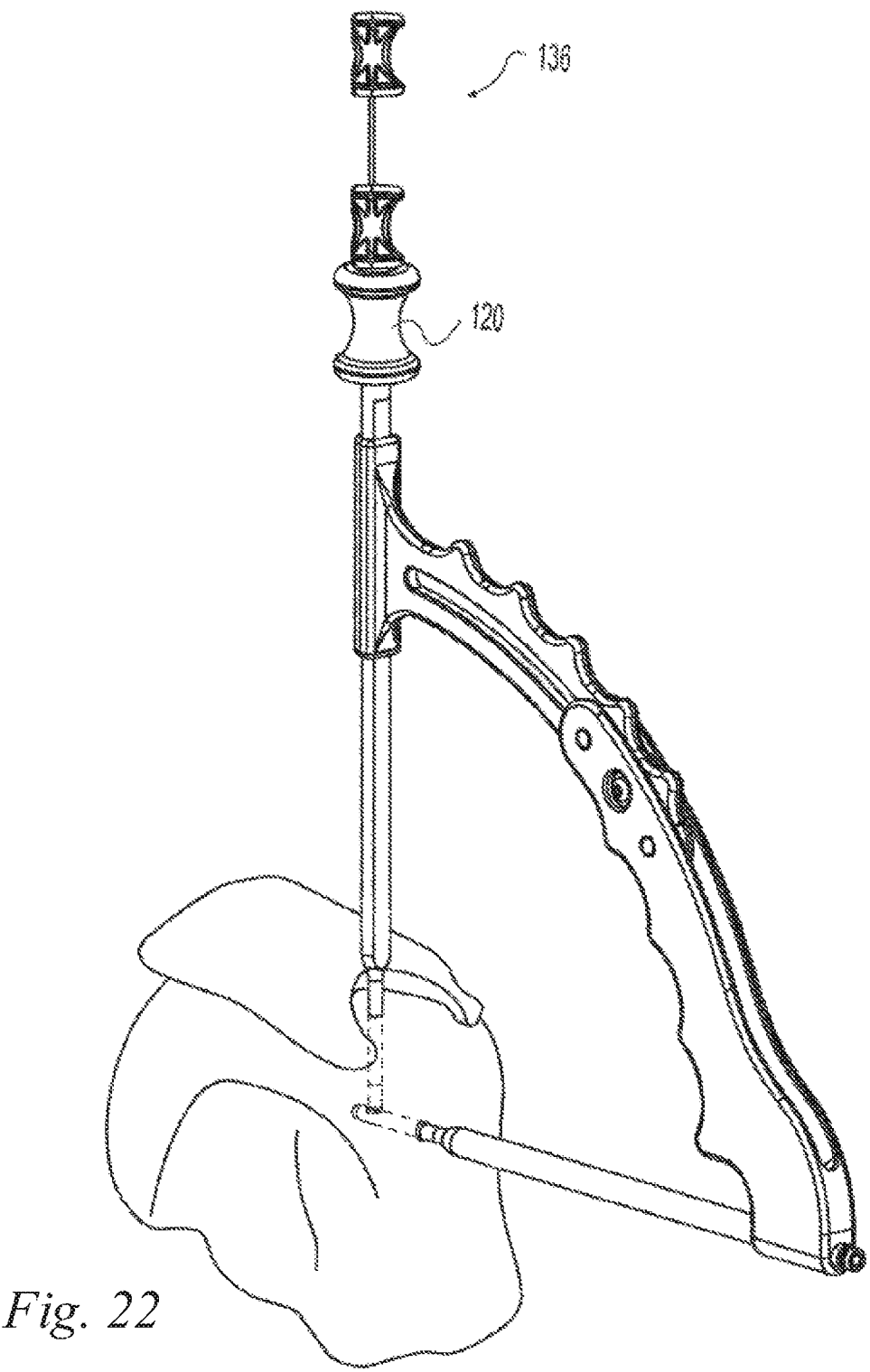

Referring to FIG. 22, the second tunnel member 120 is engaged with the first tunnel member 110 and the passer 400 inserted into the second tunnel member 120.

Figure 23:
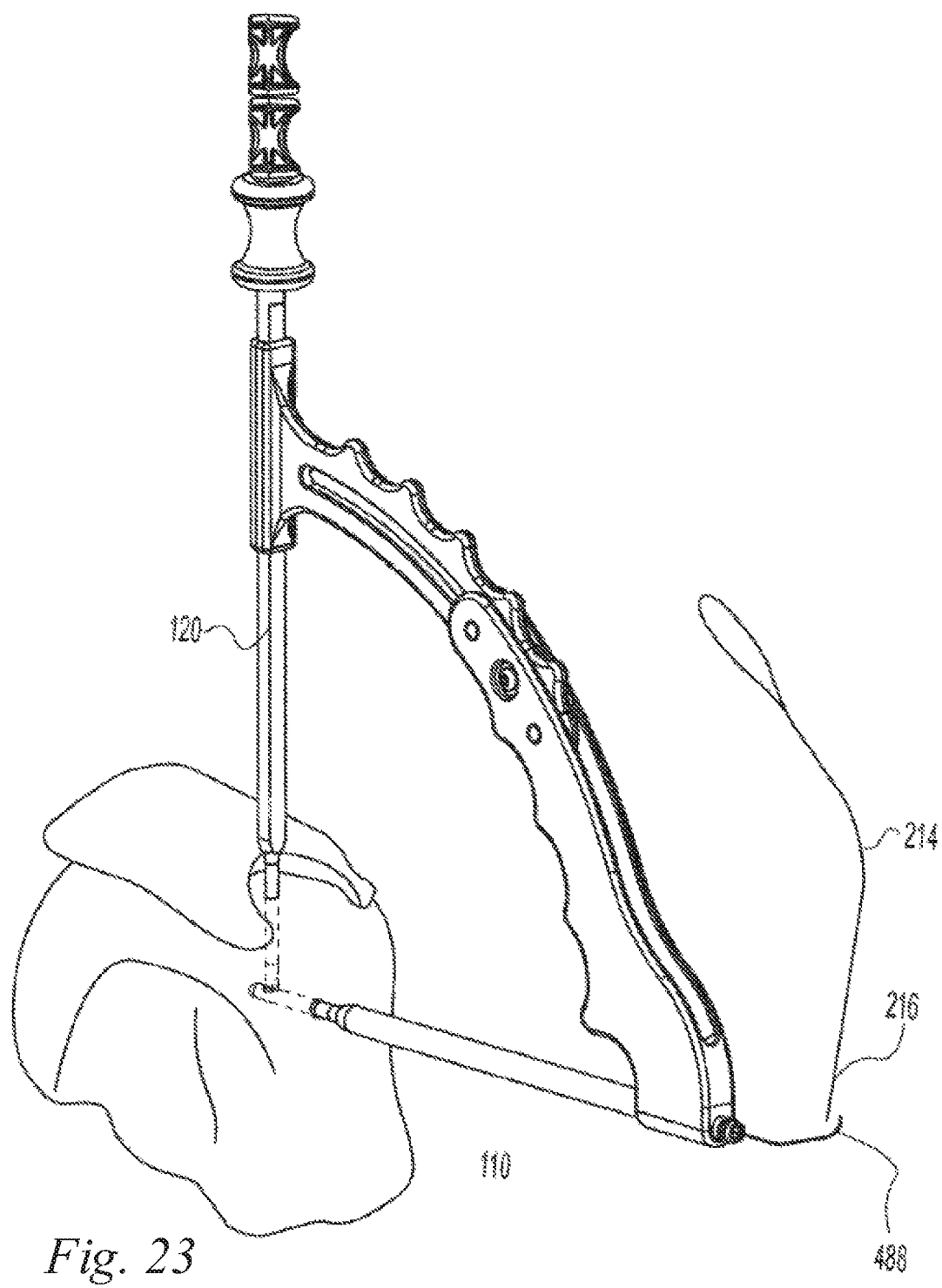

Referring to FIG. 23, the wire is advanced through the first and second tunnel members 110, 120 until it extends from the proximal end of the first tunnel member 110. The end 216 of a first shuttle suture 214 is passed through the loop 488 of the passer 400.

Figure 24:
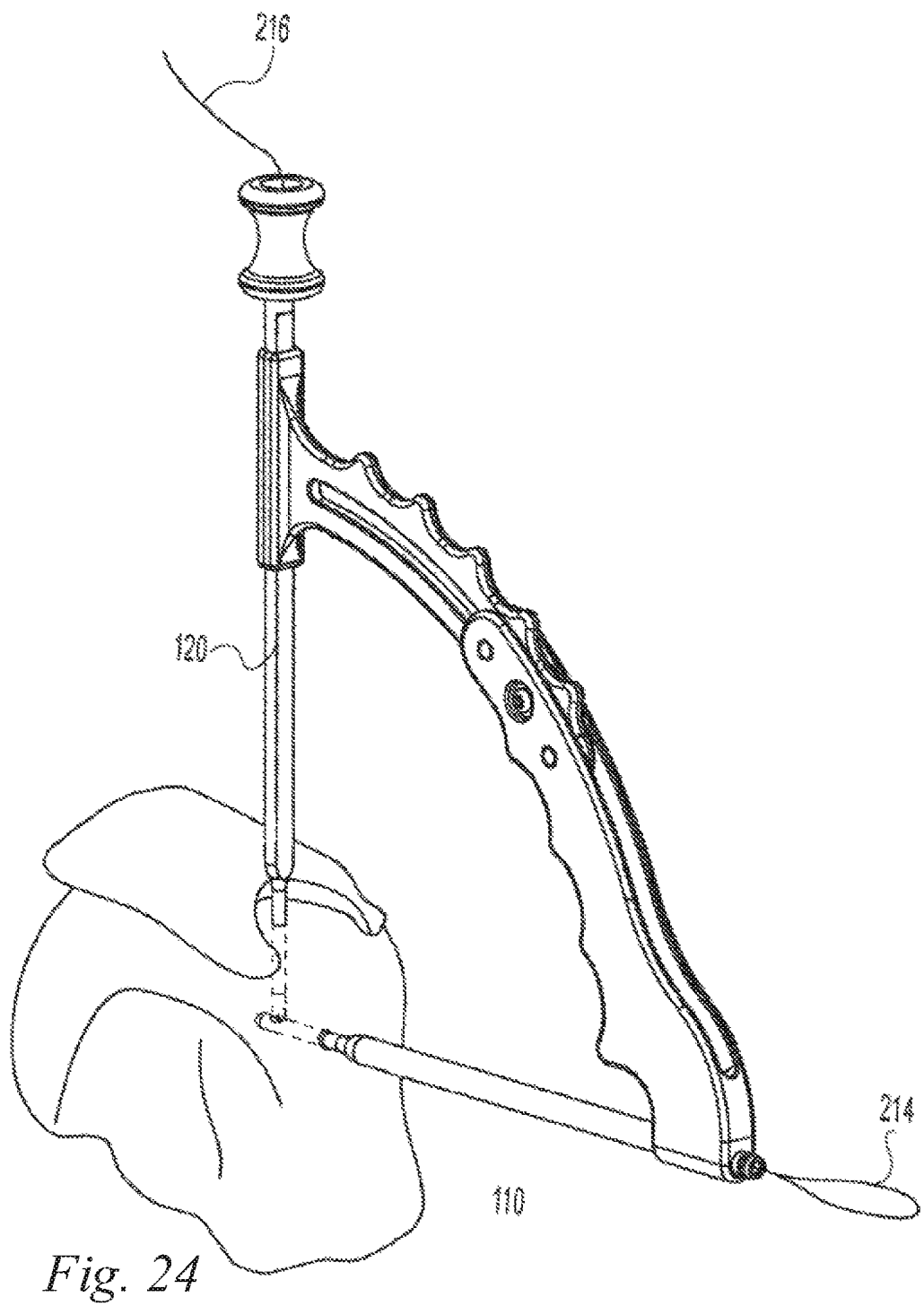

Referring to FIG. 24, the end 216 of the shuttle suture 214 is retrieved by pulling the passer 136 out the distal end of the second tunnel member 120.

Figure 25:
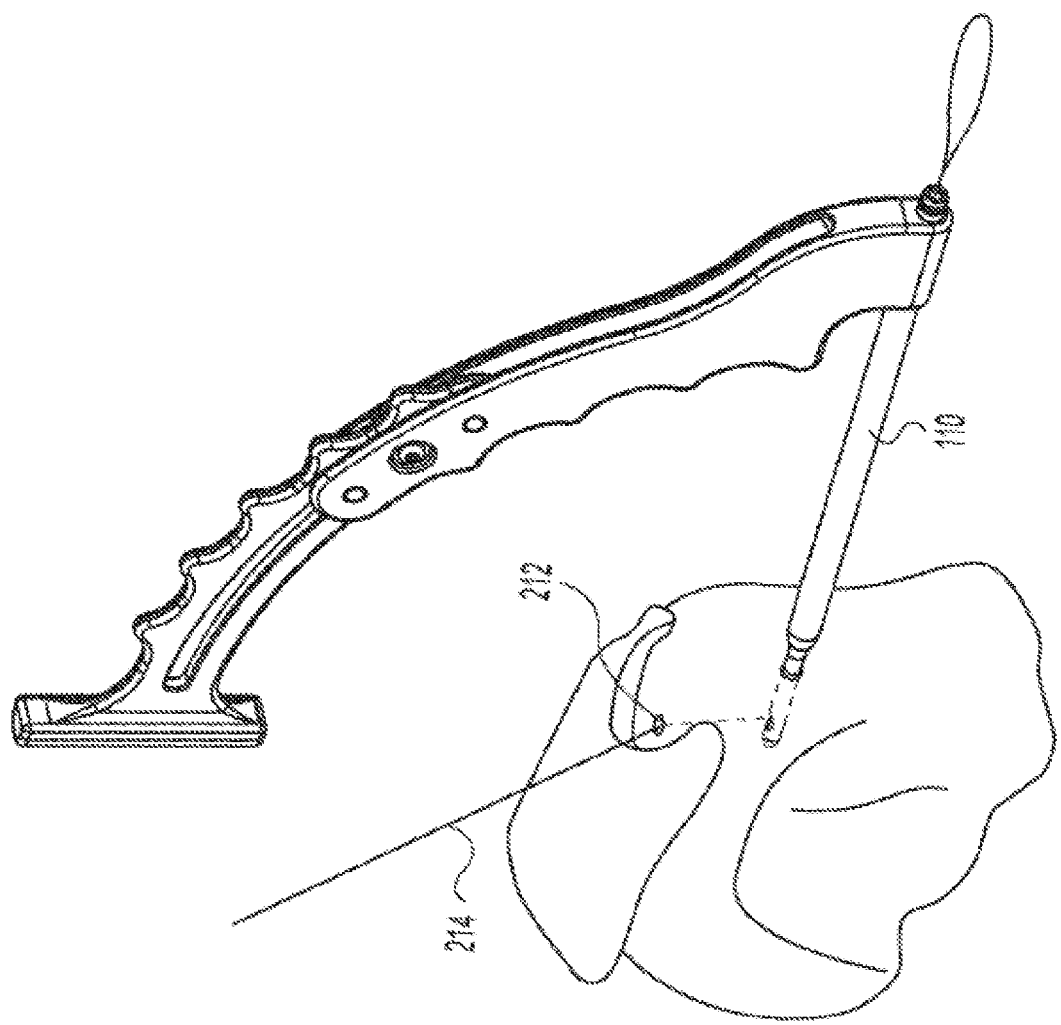

Referring to FIG. 25, the second tunnel member 120 is removed leaving the first shuttle suture 214 in place in the first tunnel member 110 and extending out of the second, medial bone tunnel 212.

Figure 26:
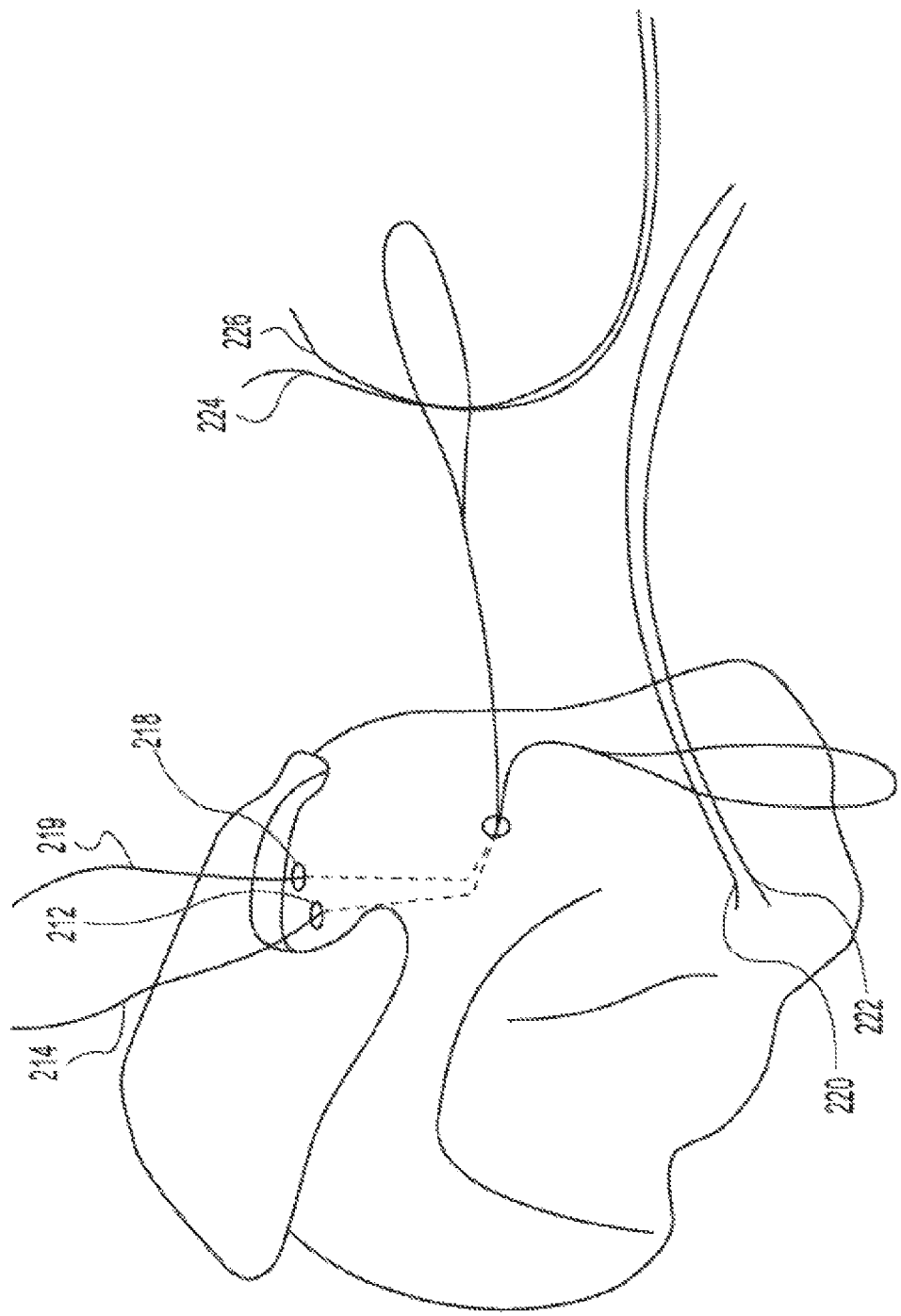
Figure 27:
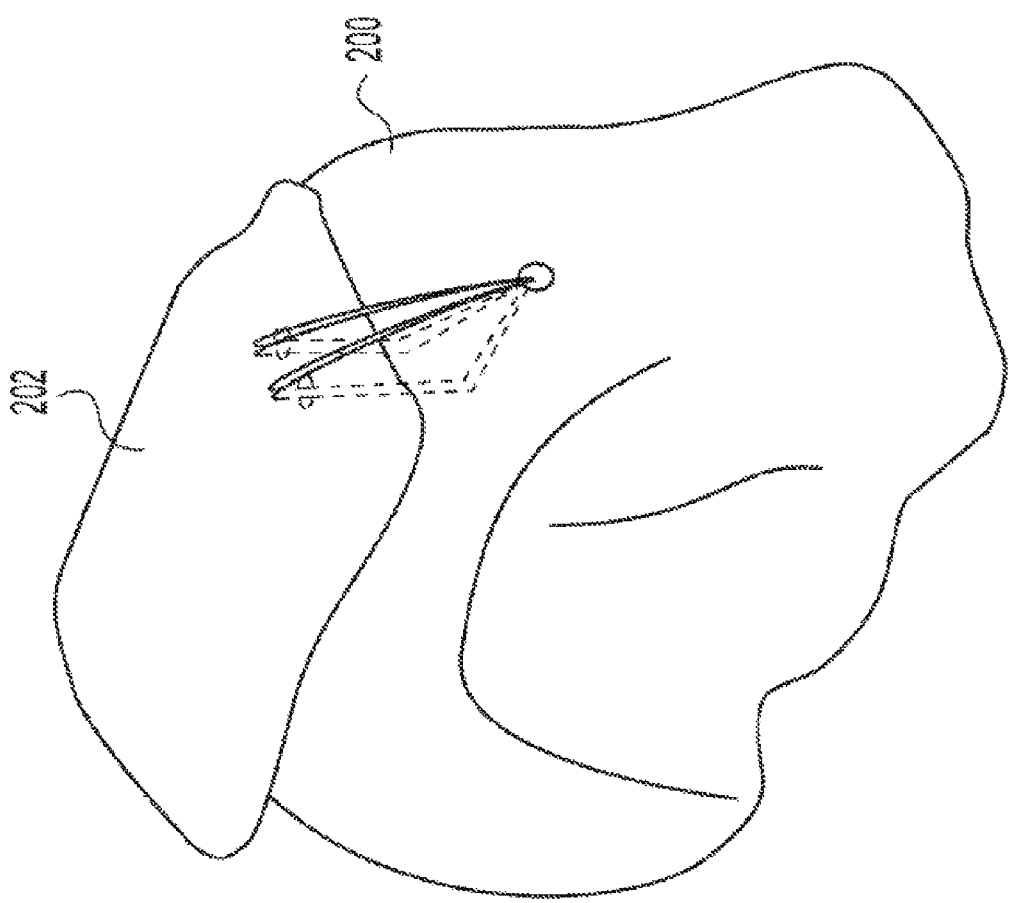

Referring to FIGS. 26 and 27, the preceding steps are repeated to create a third, additional medial, tunnel 218 and place a second shuttle suture 219 while the first tunnel member 110 remains in the bone and while the first shuttle suture 214 remains in the first tunnel member 110. Two limbs 220, 222 of a first repair suture are passed through the loop of the first shuttle suture 214 and two limbs 224, 226 of a second repair suture are passed through the loop of the second shuttle suture 219. The shuttle sutures 214, 219 are pulled to pass the limbs of the repair sutures through the bone. The repair sutures are passed through the rotator cuff 202 and used to secure it to the humerus 200.

Figure 28:
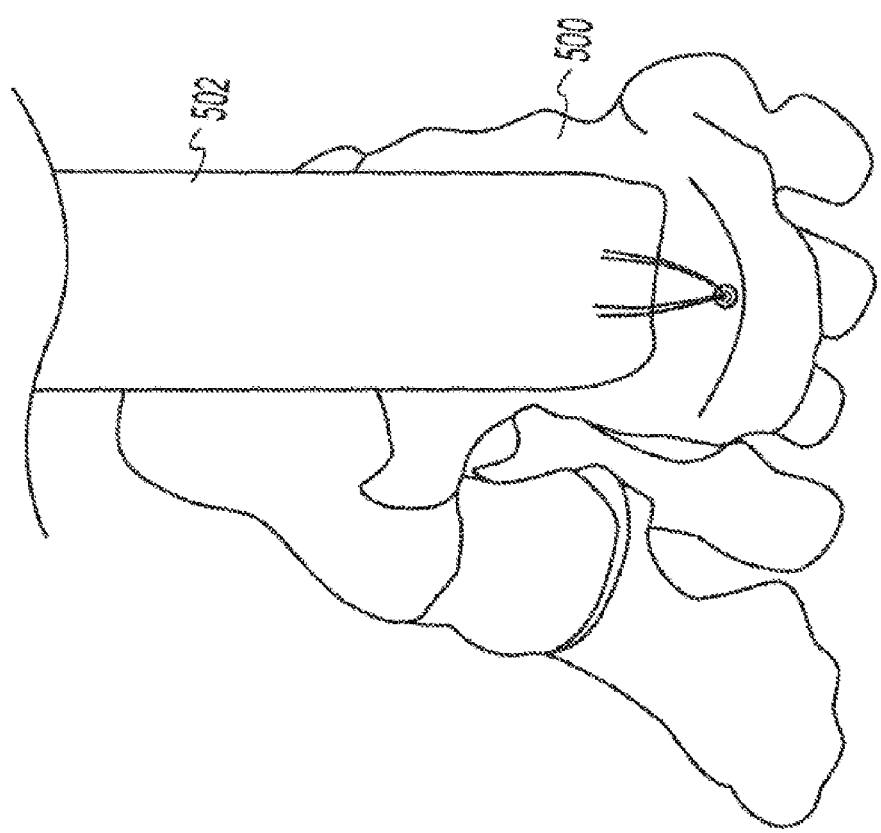
Figure 29A:
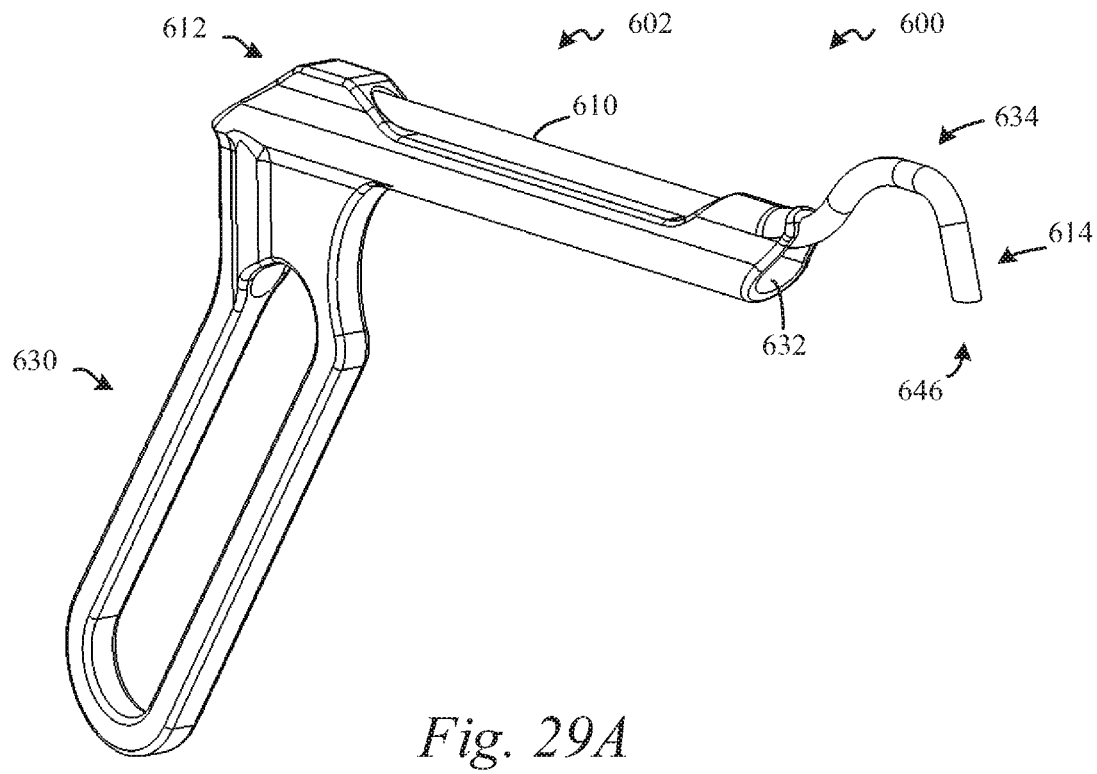
FIGS. 29A and 29B are perspective views of another example guide body of the present disclosure.
Figure 29B:
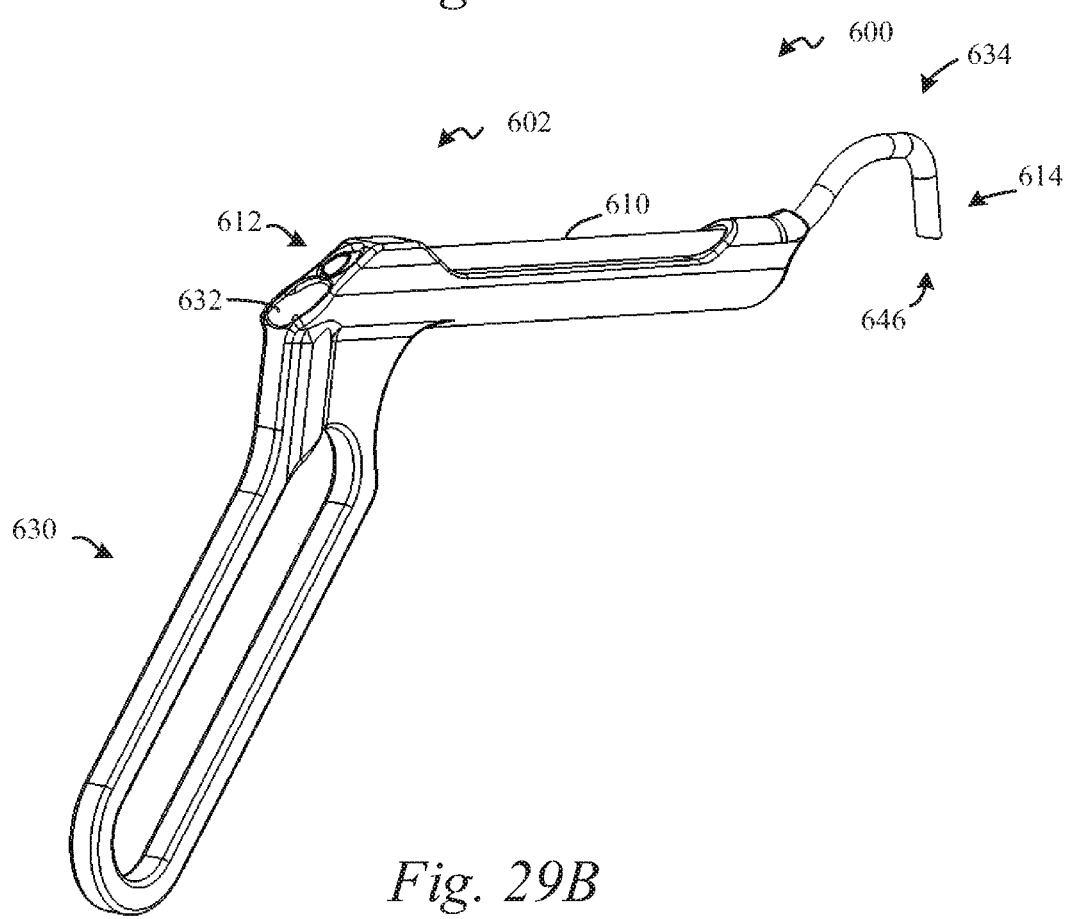
Figure 30A:
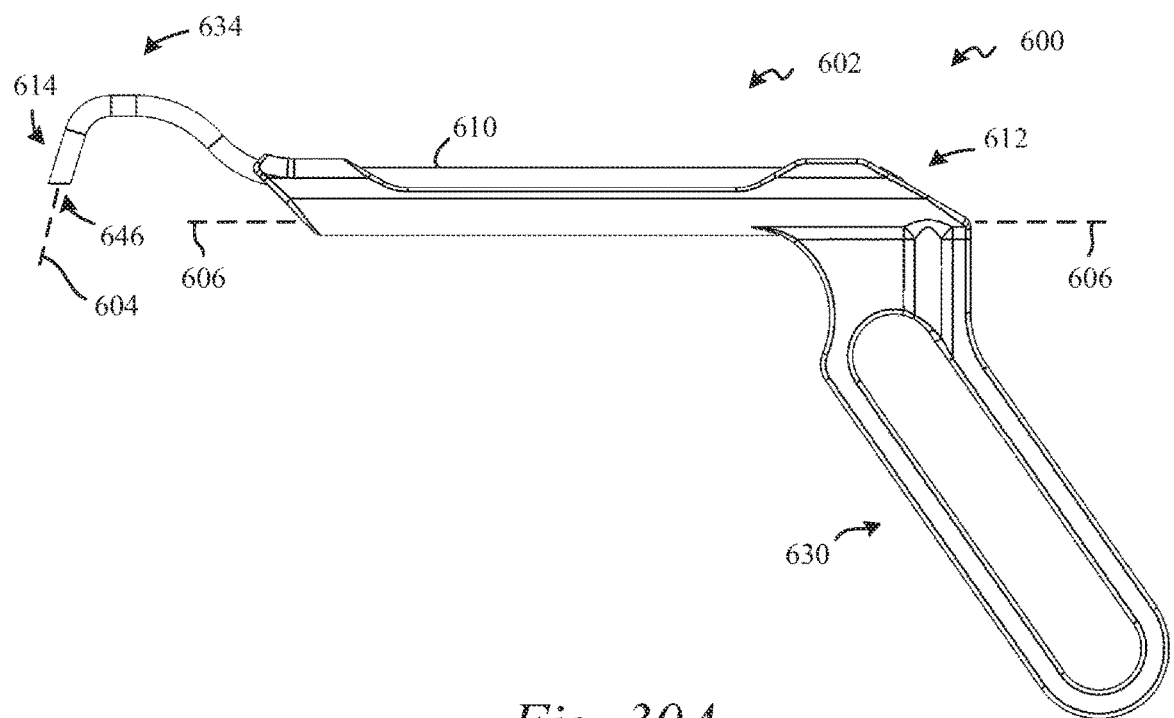
FIG. 30A is a side elevation view of the guide body of FIGS. 29A and 29B.
Figure 30B:
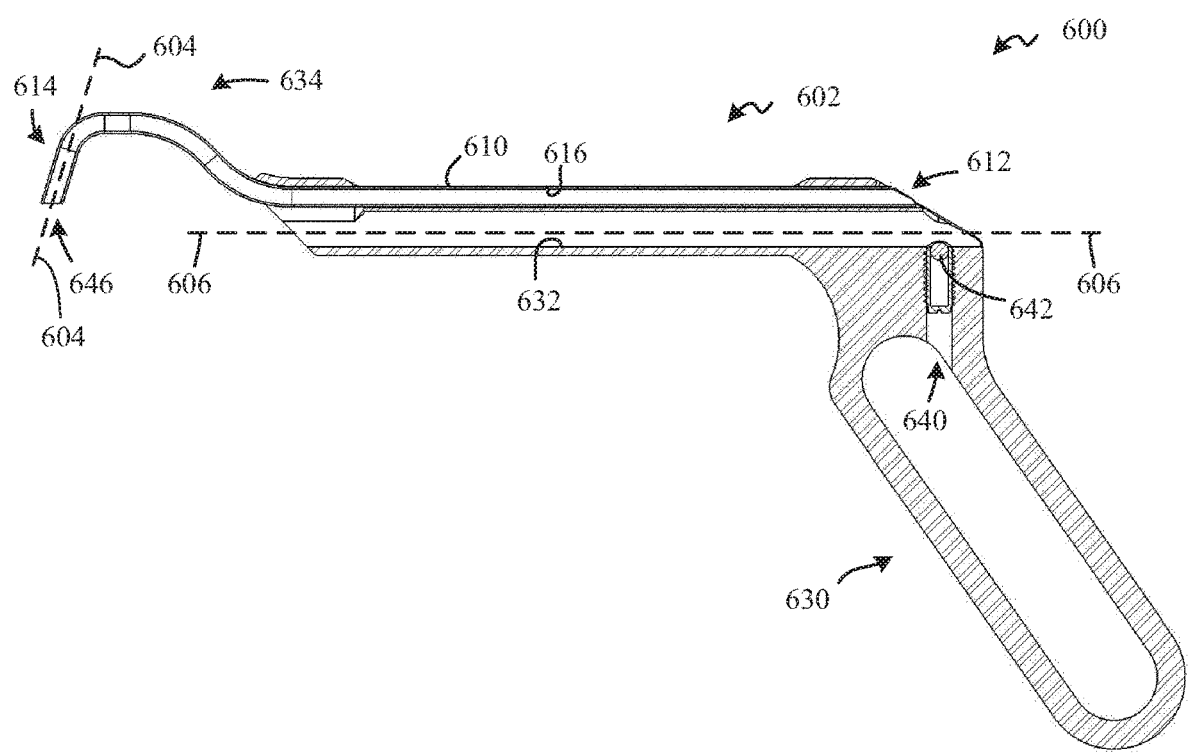
FIG. 30B is a side section view of the guide body of FIG. 30A.

Referring to FIG. 28 the instruments and methods may also be used for other repairs such as, for example, an Achilles tendon repair in which the first and second tunnel members are inserted into the heel bone 500 and one or more sutures are passed and used to secure the Achilles tendon 502 to the bone 500.

While the illustrative examples have shown bone tunnels being formed by punching instruments into the bone, it is also within the scope of the present disclosure to form bone tunnels by drilling, reaming, broaching, and/or any suitable tunnel forming process. It is contemplated, and within the scope of the present disclosure, that the various features of the illustrative examples may be interchanged among the illustrative examples.

FIGS. 29A-31C depict another example surgical instrument or guide 600 that may be used place a flexible member transosseously through first and second bone tunnels oriented transverse to each other and intersecting one other at a location within a bone. FIGS. 32-39 depict methods for placing a flexible member transosseously through first and second transverse, intersecting bone tunnels utilizing the guide 600 shown in FIGS. 29A-31C.

Referring now to FIGS. 29A-30B, the guide 600 may include a guide body 602. The guide body 602 may include a first tunnel member 610, a longitudinal guide body passage 632 (FIG. 30B), a guide body handle portion 630, and a detent mechanism 640.

The first tunnel member 610 may be engaged with the guide body 602 in a fixed fashion, or in a removably engaged fashion, and may include a proximal end 612, a distal end 614, a distal opening 646, a curved portion 634 that is nearer the distal end 614 than the proximal end 612 of the first tunnel member 610, and a first longitudinal passage 616 (FIG. 30B) that extends through the first tunnel member 610 and communicates with the distal opening 646. In one embodiment, the curved portion 634 may include a first bend 631, a second bend 633, a third bend 635, a first straight segment 636 and a second straight segment 637. However, in other embodiments (not shown) the curved portion 634 may include a single continuous bend, or any number of bends and/or any number of straight segments, without departing from the spirit or scope of the present disclosure. The distal end 614 of the first tunnel member 610 may define a first guide axis 604 and at least a portion of the first longitudinal passage 616, near the distal end 614 of the first tunnel member 610, may be coaxial with the first guide axis 604.

The longitudinal guide body passage 632 may be formed in the guide body 602 and may define a second guide axis 606. The first guide axis 604 and the second guide axis may be configured to intersect each other at a location spaced from the guide body 602 and at least a portion of the first longitudinal passage 616 near the proximal end 612 of the first tunnel member 610 may be parallel with the second guide axis 606 and/or parallel with the longitudinal guide body passage 632.

The detent mechanism 640 may be formed in the guide body handle portion 630 and may include a spring-biased ball plunger 642 that protrudes into the longitudinal guide body passage 632, as will be explained in more detail below.

Figure 31A:
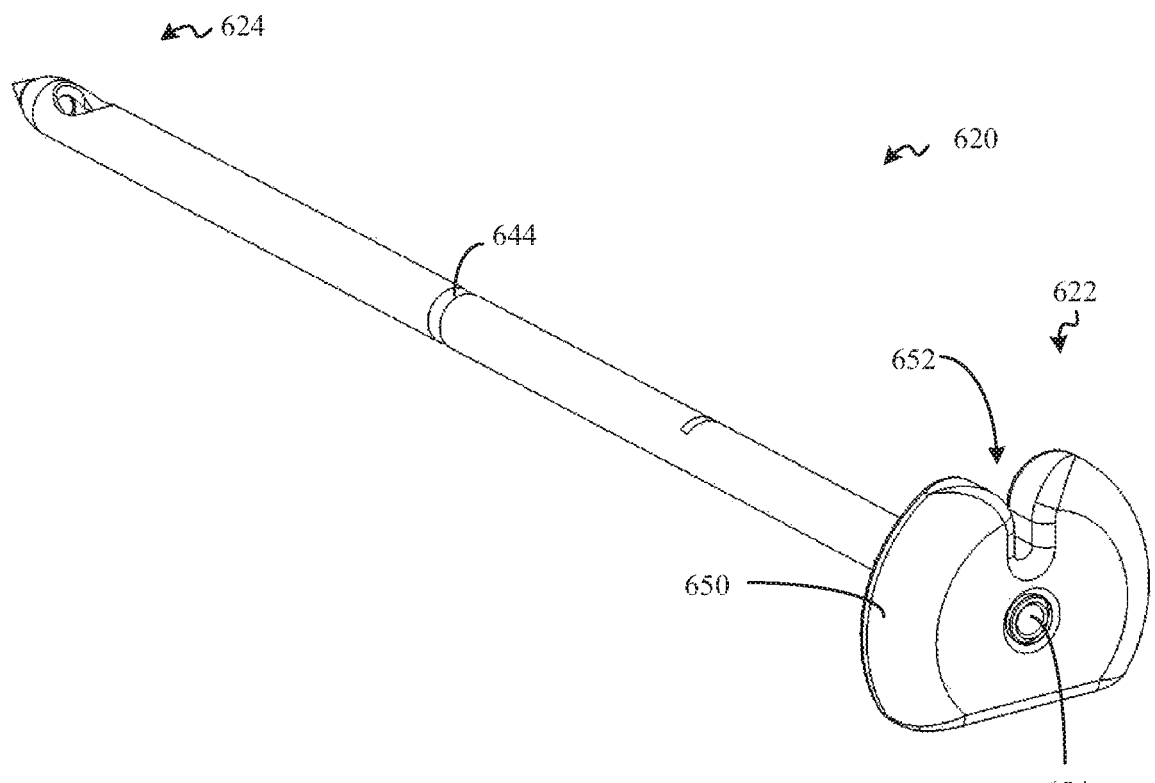
FIG. 31A is a perspective view of an example second tunnel member that may be used with the guide of FIGS. 29A-30B.
Figure 31B:
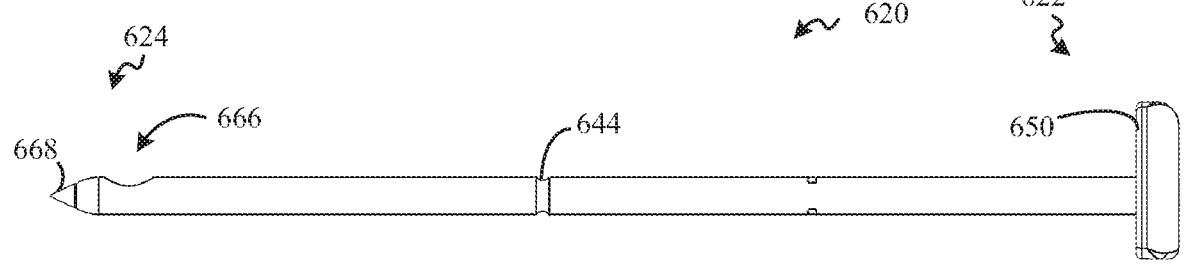
FIG. 31B is a side elevation view of the second tunnel member of FIG. 31A.
Figure 31C:
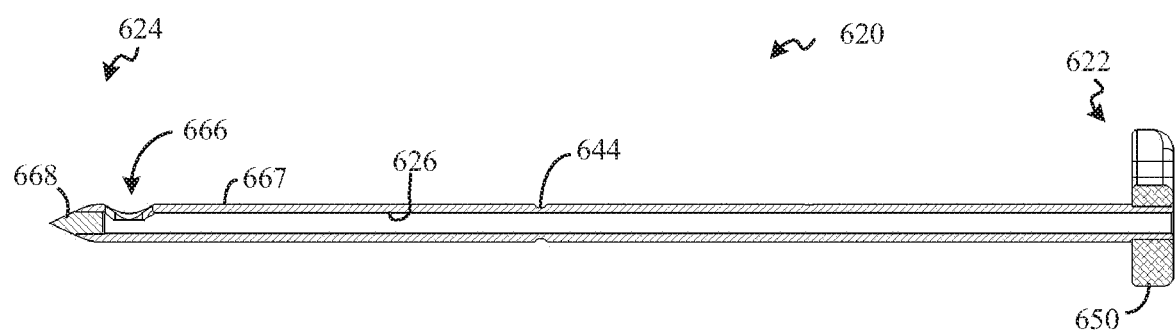
FIG. 31C is a side section view of the second tunnel member of FIG. 31B.

Referring now to FIGS. 31A-31C, the guide 600 may include a second tunnel member 620. In at least one embodiment, the second tunnel member 620 may be a bone punch that is removably engaged with the longitudinal guide body passage 632. In this manner, the second tunnel member 620 may be separable from the guide body 602 and may engage the guide body 602 in an axial sliding relationship along the second guide axis 606 within the longitudinal guide body passage 632. The second tunnel member 620 may include a proximal end 622, a distal end 624, a second longitudinal passage 626, a side wall 667, a side opening 666, a sharp point 668, an annular notch 644, a handle 650, a first aperture 652 formed in the handle 650, and a second aperture 654 formed in the handle 650.

The second longitudinal passage 626 may extend at least partway through the second tunnel member 620 and the second longitudinal passage 626 may be coaxial with the second guide axis 606 when the second tunnel member 620 is engaged within the longitudinal guide body passage 632.

As previously discussed, the detent mechanism 640 may be configured to engage and retain the second tunnel member 620 in a desired axial position relative to the guide body 602, causing the second tunnel member 620 to resist axial movement along the second guide axis 606. The annular notch 644 that is formed in the side wall 667 of the second tunnel member 620 may have a complementary shape that interacts with the spring-biased ball plunger 642 of the detent mechanism 640 to resist axial sliding of the second tunnel member 620 within the longitudinal guide body passage 632. This feature may help prevent the second tunnel member 620 from accidentally falling out of the longitudinal guide body passage 632 as the guide 600 is moved about during surgical procedures. The spring-biased ball plunger 642 may achieve this function by engaging within the annular notch 644 and resisting axial sliding of the second tunnel member 620 due to a spring-biased forced that is placed upon the ball plunger. However, the surgeon can still freely rotate the second tunnel member 620 within the longitudinal guide body passage 632 because the spring-biased ball plunger 642 will remain within the annular notch 644 as the second tunnel member 620 is rotated within the longitudinal guide body passage 632. Moreover, sufficient axial force may be applied to the second tunnel member 620 to overcome the force of the spring-biased ball plunger 642 and eject the spring-biased ball plunger 642 from within the annular notch 644 and freely slide the second tunnel member 620 axially within longitudinal guide body passage 632.

The side opening 666 may be formed in the side wall 667 nearer the distal end 624 of the second tunnel member 620 than the proximal end 622 of the second tunnel member 620. The second longitudinal passage 626 may extend from the proximal end 622 of the second tunnel member 620 toward the distal end 624 of the second tunnel member 620 and may communicate with the side opening 666. The side opening 666 formed in the second tunnel member 620, and the distal opening 646 of the first tunnel member 610, may be in communication with each other when the second tunnel member 620 is axially translated such that the first guide axis 604 intersects the side opening 666 of the second tunnel member 620.

Figure 35:
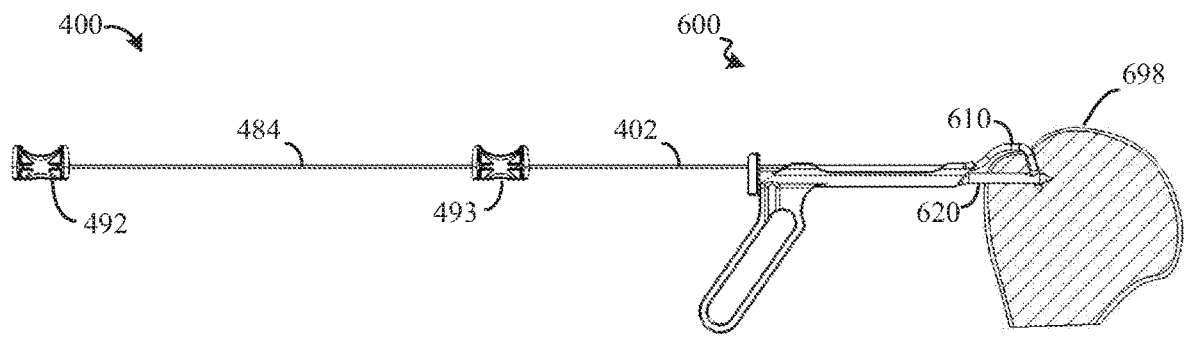
FIG. 35 is a side elevation view of the guide of FIGS. 29A-31C engaged with the bone of FIG. 32 and a passer inserted into the first tunnel member.
Figure 36:
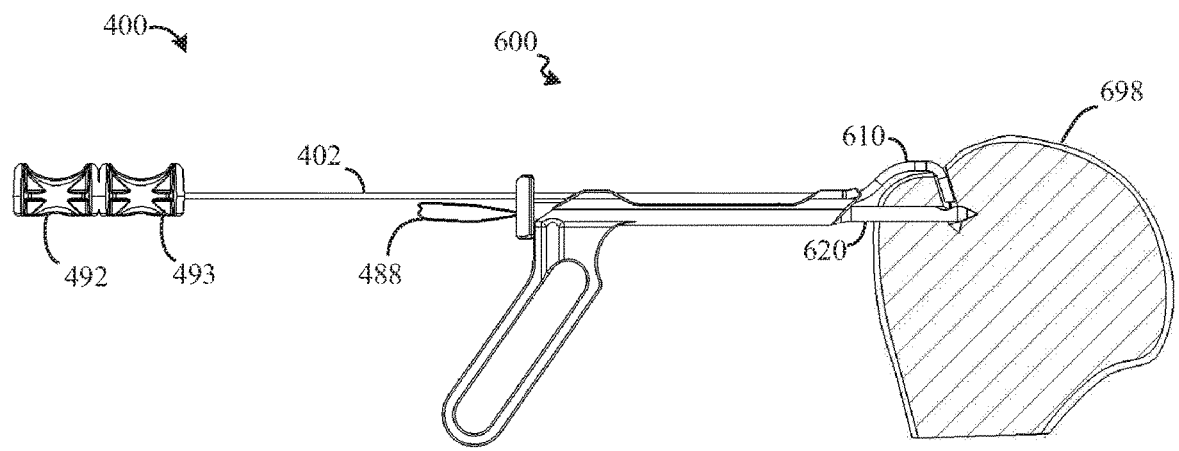
FIG. 36 is a side elevation view of the guide of FIGS. 29A-31C engaged with the bone of FIG. 32 with a passer wire threaded through both tunnel members and protruding from the proximal end of the second tunnel member.
Figure 37:
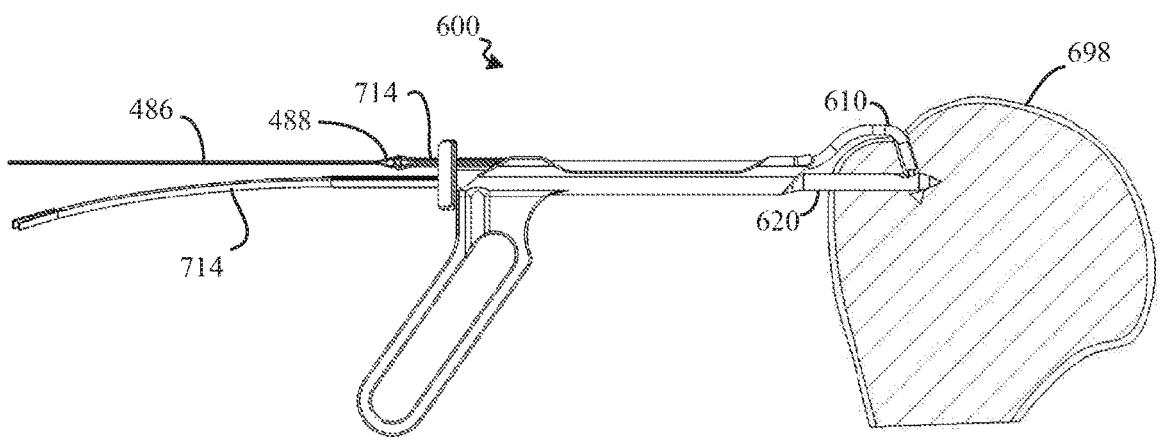
FIG. 37 is a side elevation view of the guide of FIGS. 29A-31C engaged with the bone of FIG. 32 with a first flexible member engaged with the passer wire and pulled through both tunnel members.

FIGS. 35-37 show how the guide 600 may be used with a passer, such as the passer 400 shown in FIGS. 12-13. The passer 400 may be operable to extend from the proximal end 612 of the first tunnel member 610, through the distal end 614 of the first tunnel member 610, through the distal end 624 of the second tunnel member 620, and to the proximal end 622 of the second tunnel member 620 in one continuous path. The passer 400 may then be used to pull a flexible member 714 such as, for example, a passing suture or a repair suture through the tunnel members 610, 620 to pass the flexible member 714 through the bone 698.

FIGS. 32-38 illustrate an example of a surgical method according to the present disclosure. In the illustrative example of FIGS. 32-38, instruments and methods of the previous examples are shown in use to place transosseous sutures to repair a rotator cuff of a shoulder joint. However, it will be understood that any of the examples of instruments and methods of the present disclosure may be used in any combination to pass a member through a shoulder bone or other bones at a shoulder or other surgical sites and for rotator cuff repair and/or other surgical purposes.

Figure 32:
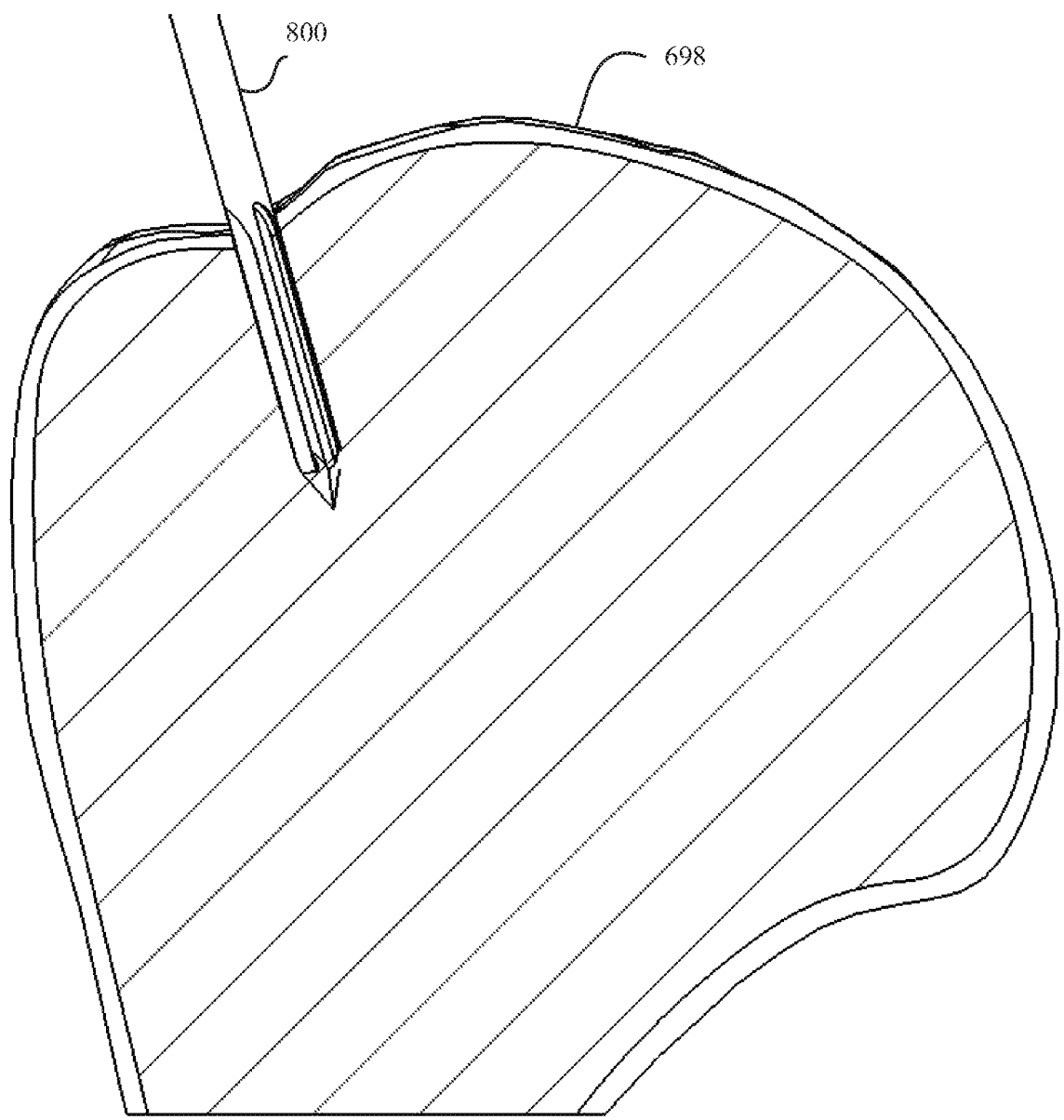
FIG. 32 is a side section view of a bone with a punch inserted into the bone to form a first bone tunnel.

Referring to FIG. 32, a tool 800, such as a medial bone punch, a bone drill, etc., may be used to form a first bone tunnel in the bone 698.

Figure 33:
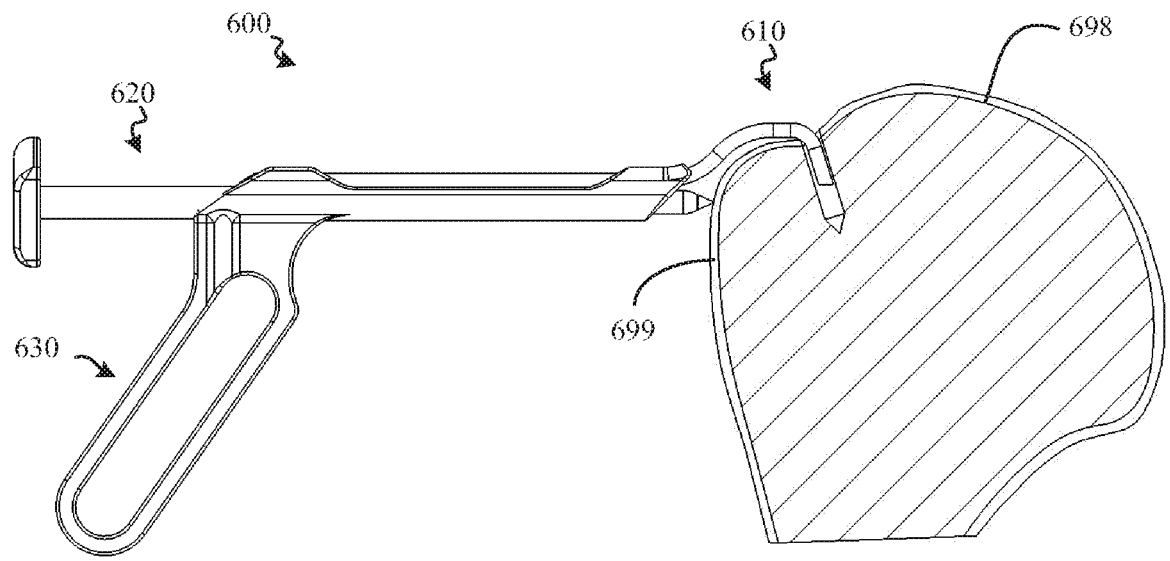
FIG. 33 is a side elevation view of the guide of FIGS. 29A-31C engaged with the bone of FIG. 32 and a first tunnel member inserted into the first bone tunnel.

Referring to FIG. 33, the guide 600 may be placed proximal the bone 698 with the distal end 614 of the first tunnel member 610 inserted into the first bone tunnel that was formed by the tool 800 in FIG. 33. The guide 600 may be rotated back and forth, and pitched up and down, while the first tunnel member 610 is inserted into the first bone tunnel to position the sharp point 668 of the second tunnel member 620 at the desired location on the surface of the bone 698 before punching the second bone tunnel into the bone 698 using the second tunnel member 620. For example, the desired location of the sharp point 668 of the first tunnel member 110 on the surface of the bone 698 may be on the lateral surface of the greater tuberosity 699 of the humerus approximately 30 mm inferior to the superior border of the tuberosity. The guide 600 may be oriented such that it is perpendicular to the long axis of the humerus and perpendicular to the acromion (not shown).

Figure 34:
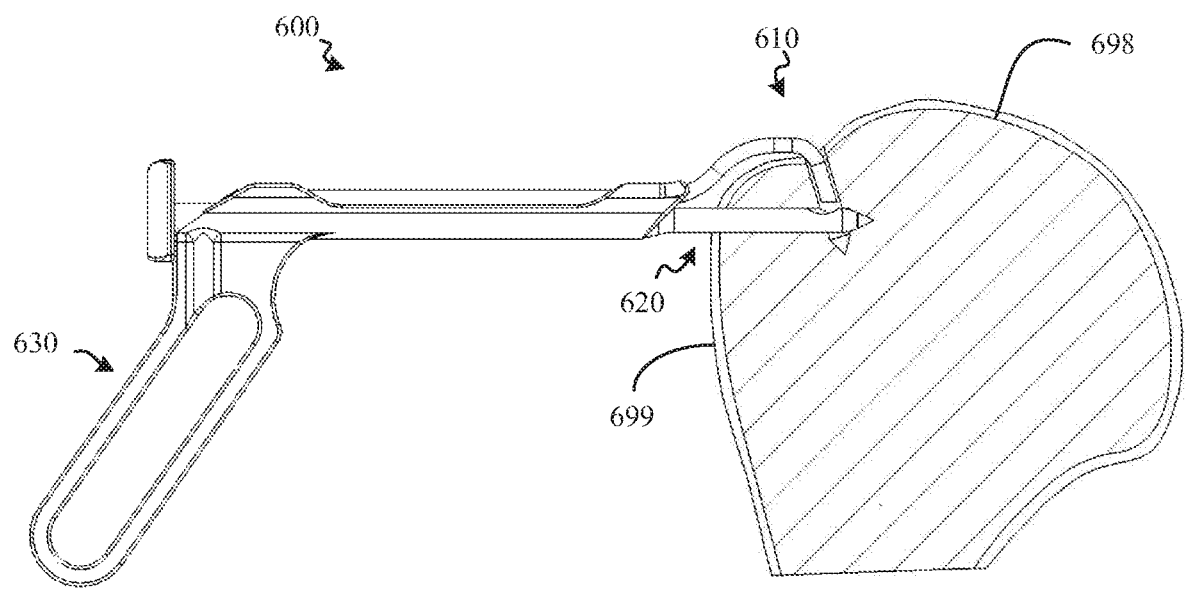
FIG. 34 is a side elevation view of the guide of FIGS. 29A-31C engaged with the bone of FIG. 32 and the second tunnel member inserted into the bone.

Referring to FIG. 34, the second tunnel member 620 may be impacted into the bone 698 to form the second bone tunnel. The second tunnel member 620 may also be rotated/oriented to engage the distal opening 646 of the first tunnel member 610 with the side opening 666 of the second tunnel member 620, such that the distal opening 646 of the first tunnel member 610 and the side opening 666 of the second tunnel member 620 are in communication with each other.

Referring to FIG. 35, the passer 400 may be inserted into the proximal end 612 of the first tunnel member 610.

Referring to FIG. 36, the wire 486 of the passer 400 may be advanced through the first tunnel member 610, into the second tunnel member 620, and then further advanced until the bent loop 488 on the end of the wire 486 protrudes from the proximal end 622 of the second tunnel member 620.

Referring to FIG. 37, the first flexible member 714 may be passed through the bent loop 488 of the wire 486, to engage the first flexible member 714 with the passer 400, and the first flexible member 714 may then be threaded through the tunnel members 610, 620 (and the bone tunnels) by pulling the wire 486 out of the proximal end 612 of the first tunnel member 610.

Figure 38:
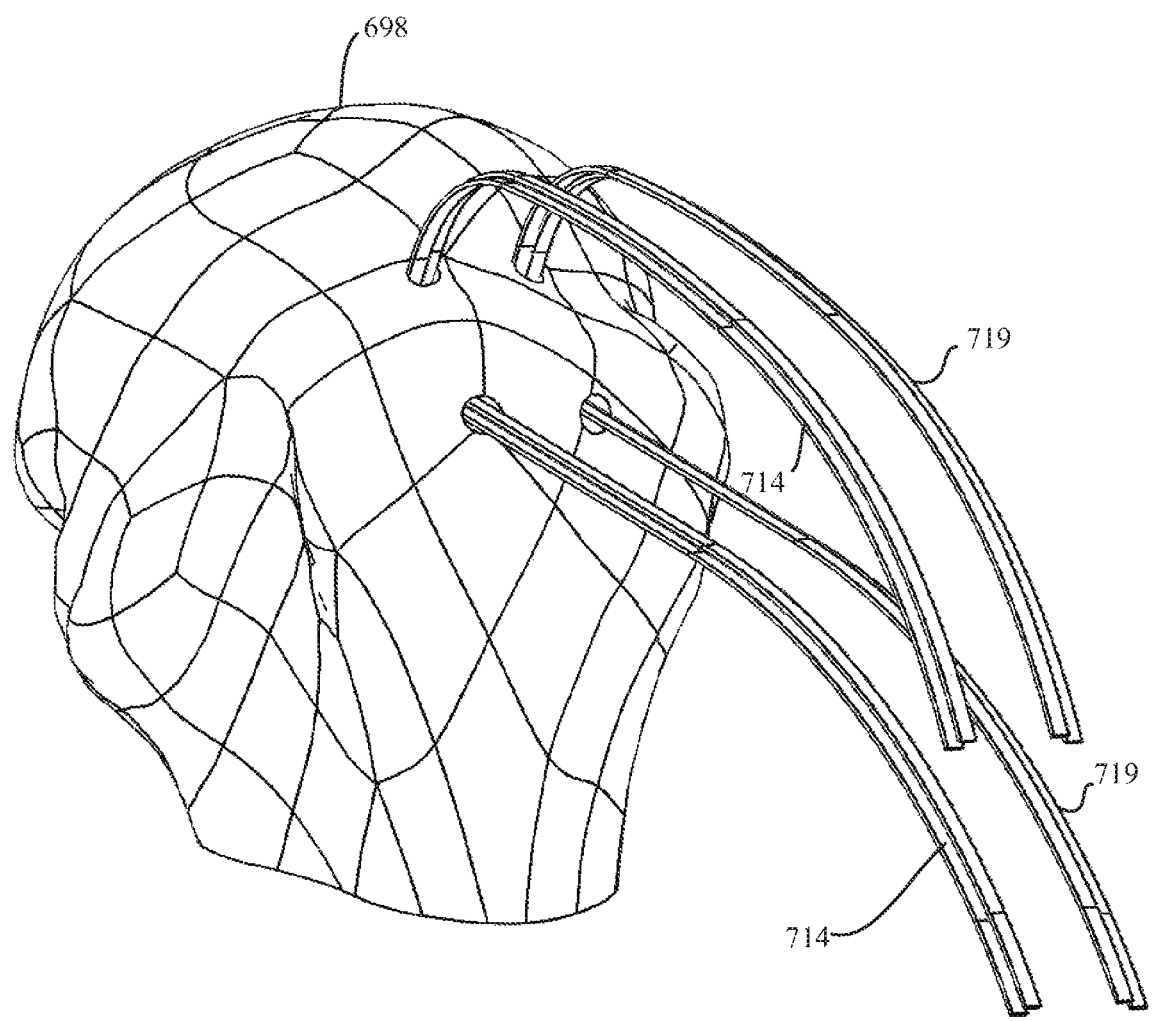
FIG. 38 is a perspective view of a bone with first and second flexible members passed through the bone.

Referring to FIG. 38, the first tunnel member 610 and the second tunnel member 620 are removed from the bone tunnels, along with the guide 600, leaving the first flexible member 714 in place in the bone 698. Moreover, the preceding steps may be repeated to create additional bone tunnels and place a second flexible member 719 (or more flexible members, as desired), as shown in FIG. 38.

Figure 39:
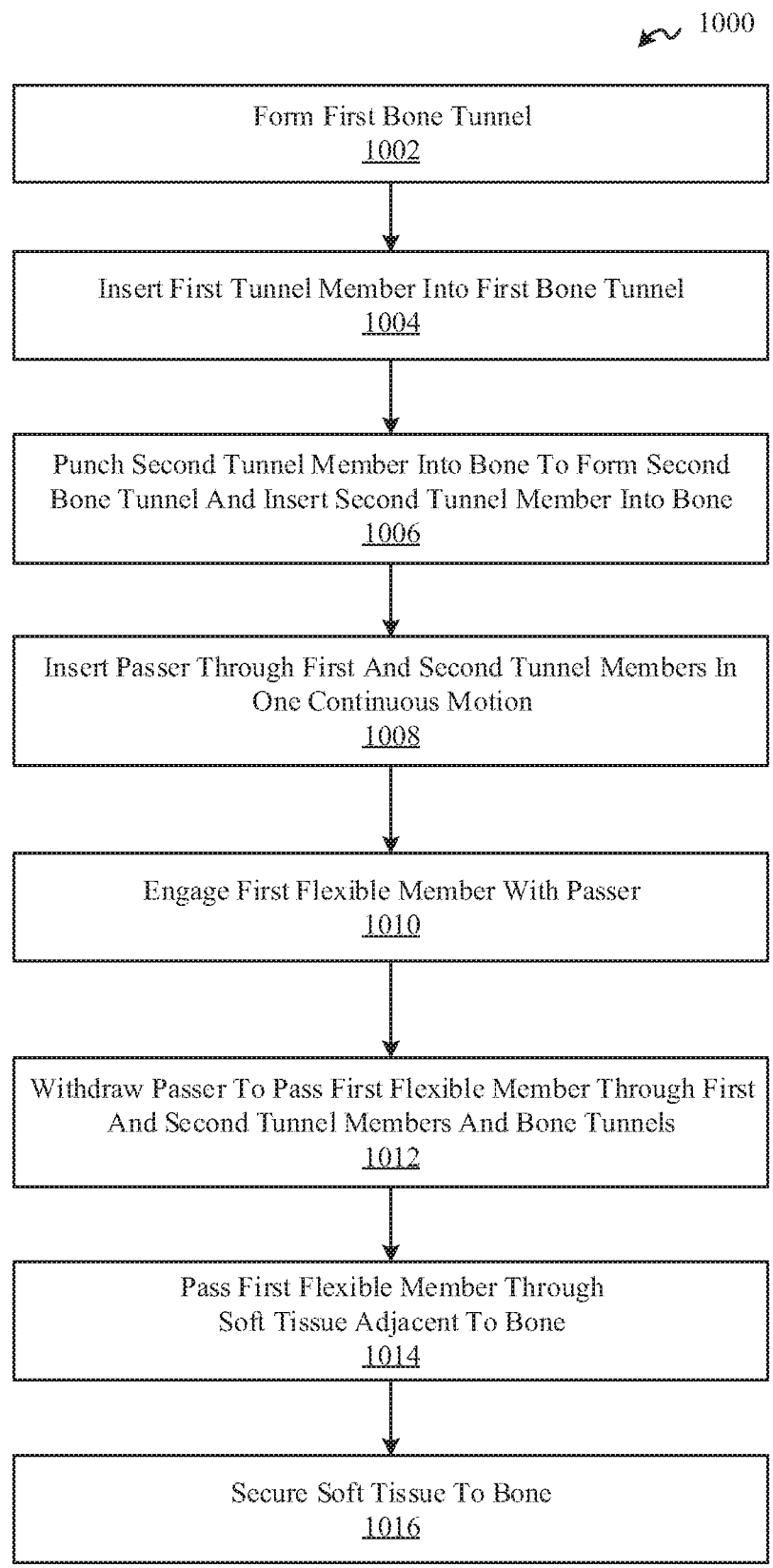
FIG. 39 is a flowchart diagram illustrating a method of placing a flexible member transosseously through first and second transverse, intersecting bone tunnels.

Referring now to FIG. 39, a flowchart diagram is shown of a method 1000 of placing a flexible member transosseously through first and second transverse, intersecting bone tunnels, according to embodiments of the present disclosure. The method 1000 may be carried out through the use of any of the surgical instruments of FIGS. 1-37. Alternatively, the method 1000 may be carried out with surgical instruments different from those shown in FIGS. 1-37 and/or described elsewhere herein.

The method 1000 may begin with a step 1002, in which a first bone tunnel may be formed in a bone 698. The first bone tunnel may be sized and configured to receive a first tunnel member 610 therein.

The method 1000 may then proceed to a step 1004, in which a first tunnel member 610 may be inserted into the first bone tunnel of the bone 698 along a first insertion axis 604. The first tunnel member 610 may include a proximal end 612, a distal end 614, and a first longitudinal passage 616 extending through the first tunnel member 610.

The method 1000 may then proceed to a step 1006, in which a second tunnel member 620 may be inserted into the bone 698 along a second insertion axis 606 and the second insertion axis 606 may intersect the first insertion axis 604. The second tunnel member 620 may be punched into the bone 698 to form a second bone tunnel and insert the second tunnel member 620 into the bone 698 along the second insertion axis 606 after the first tunnel member 610 has been inserted into the first bone tunnel. The second tunnel member 620 may include a proximal end 622, a distal end 624, and a second longitudinal passage 626 extending at least partway through the second tunnel member 620.

The method 1000 may then proceed to a step 1008, in which a passer 400 may be inserted through the first and second tunnel members 610, 620 in one continuous motion until the passer 400 extends through the first longitudinal passage 616, the second longitudinal passage 626, out of the proximal end 612 of the first tunnel member 610, and out of the proximal end 622 of the second tunnel member 620.

In other words, the passer 400 may be inserted through the first and second tunnel members 610, 620 by inserting the passer 400 so that it extends between the proximal end 612 of the first longitudinal passage 616, the distal end 614 of the first longitudinal passage 616, the distal end 624 of the second longitudinal passage 626, and the proximal end 622 of the second longitudinal passage 626 by advancing the passer 400 into the proximal end 612 of the first tunnel member 610, along the first longitudinal passage 616, through a distal opening 646 in the first tunnel member 610, through a side opening 666 in the second tunnel member 620, along the second longitudinal passage 626, and out a proximal end 622 of the second tunnel member 620 in one continuous motion.

The passer 400 may also include a wire 486 forming a loop 488 in a first plane, the loop 488 being bent so that a portion of the loop 488 forms a curved profile in a second plane perpendicular to the first plane and an outer tube 402 that is moveable relative to the wire 486 between a first position in which the outer tube 402 encloses a portion of a length of the wire 486 and a second position in which the outer tube 402 encloses less of the length of the wire 486. The wire 486 may be inserted into the first tunnel member 610 while the outer tube 402 is positioned in the first position and the outer tube 402 may be subsequently moved to the second position to pass the loop 488 from the distal opening 646 in the first tunnel member 610 through the side opening 666 in the second tunnel member 620 and out the proximal end 622 of the second tunnel member 620.

The method 1000 may then proceed to a step 1010, in which a first flexible member 714 may be engaged with the loop 488 of the passer 400.

The method 1000 may then proceed to a step 1012, in which the passer 400 may be withdrawn from the proximal end 612 of the first tunnel member 610 to pass the first flexible member 714 through the first and second tunnel members 610, 620 and the first and second bone tunnels.

The method 1000 may then proceed to a step 1014, in which the first flexible member 714 may be passed through soft tissue (not shown) adjacent to the bone 698.

The method 1000 may then proceed to a step 1016, in which the first flexible member 714 may then be used to secure the soft tissue to the bone 698.

Alternatively, or in addition thereto, the method 1000 may proceed to a step 1018, in which the soft tissue may be secured to the bone 698 by inserting a knotless anchor (not shown) into the first bone tunnel and securing the first flexible member 714 with the knotless anchor, and the method 1000 may end.

All methods disclosed herein may be implemented in a wide variety of ways. Although the various steps of the methods disclosed herein are shown and described in a certain order, those of skill in the art will recognize that the steps of the methods disclosed herein may be executed in many different order combinations from those set forth in the descriptions of their corresponding Figures. Furthermore, some of the steps of the methods disclosed herein are optional and may be omitted and/or replaced with other steps not specifically described herein.

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the preceding detailed description of the embodiments of the apparatus, system, and method, as represented in the Figures, is not intended to limit the scope of the disclosure, as claimed, but is merely representative of exemplary embodiments of the disclosure.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Recitation in the claims of the term "first" with respect to a feature or element does not necessarily imply the existence of a second or additional such feature or element. Elements recited in means-plus-function format are intended to be construed in accordance with 35 U.S.C. § 112 paragraph 6. It will be apparent to those having skill in the art that changes may be made to the details of the above-described embodiments without departing from the underlying principles of the disclosure.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure disclosed herein without departing from the spirit and scope of the disclosure.

What is claimed is:

1. A system for placing a flexible member transosseously through first and second bone tunnels, the first and second bone tunnels oriented transverse to each other and intersecting one other, the system comprising:
   a guide body having a guide body handle portion;
   a first tunnel member engaged with the guide body, the first tunnel member having:
      a proximal end;
      a distal end;
      a first longitudinal passage extending at least partway through the first tunnel member; and
      a first guide axis associated with the distal end of the first tunnel member, wherein at least a portion of the first longitudinal passage near the distal end of the first tunnel member is coaxial with the first guide axis;
   a second tunnel member engaged with the guide body, the second tunnel member having:
      a proximal end;
      a distal end; and
      a second longitudinal passage extending at least partway through the second tunnel member; and
      a second guide axis associated with the distal end of the second tunnel member, wherein at least a portion of the second longitudinal passage near the distal end of the second tunnel member is coaxial with the second guide axis; and
   a passer comprising a suture gripper operable to hold a suture and pull the suture from the proximal end of the first tunnel member, through the distal end of the first tunnel member, through the distal end of the second tunnel member, and to the proximal end of the second tunnel member.

2. The system of claim 1 wherein the second tunnel member comprises a bone punch that is separable from the guide body and engages the guide body in axial sliding relationship along the second guide axis.

3. The system of claim 2 wherein the guide body further comprises a detent mechanism configured to engage and retain the second tunnel member in a desired axial position relative to the guide body causing the second tunnel member to resist axial movement along the second guide axis.

4. The system of claim 1, wherein the second tunnel member comprises:
   a side wall; and
   a side opening formed in the side wall nearer the distal end of the second tunnel member than the proximal end of the second tunnel member, the second longitudinal passage extending from the proximal end of the second tunnel member toward the distal end of the second tunnel member and communicating with the side opening.

5. The system of claim 4 wherein the first tunnel member is fixed to the guide body and the first tunnel member comprises a distal opening, the first longitudinal passage communicating with the distal opening, and the side opening formed in the second tunnel member and the distal opening of the first tunnel member are in communication with each other when the first guide axis intersects the side opening, and wherein at least a portion of the first longitudinal passage near the proximal end of the first tunnel member is parallel to the second guide axis.

6. The system of claim 1 wherein the passer comprises:
   a first end; and
   a second end;
   wherein the suture gripper comprises a bent loop at the second end of the passer, the passer having a length greater than a combined length of the first and second longitudinal passages.

7. The system of claim 6 wherein the passer further comprises:
   a shaft;
   a wire extending from the shaft, the shaft extending away from the first end, the shaft having a shaft length, the shaft being relatively rigid compared to the wire, the wire being attached to an end of the shaft and extending away from the shaft to the second end where the wire defines the bent loop at the second end of the passer, the wire extending from the shaft a wire length, the wire being relatively flexible compared to the shaft; and
   an outer tube engaged with the shaft in axial sliding relationship and moveable relative to the shaft from a first position in which the outer tube encloses a portion of the wire length and a second position in which the outer tube encloses less of the wire length.

8. A system for placing a member transosseously through first and second bone tunnels, the system comprising:
   a guide body having a longitudinal guide body passage;
   a first tunnel member engaged with the guide body, the first tunnel member having:

a proximal end;
a distal end; and
a first longitudinal passage extending through the first tunnel member;
a second tunnel member engaged with the longitudinal guide body passage, the second tunnel member having:
a proximal end;
a distal end; and
a second longitudinal passage extending at least partway through the second tunnel member; and
a passer operable to pass a suture from the proximal end of the first tunnel member, through the distal end of the first tunnel member, through the distal end of the second tunnel member, and to the proximal end of the second tunnel member;
wherein the passer comprises:
a first end;
a second end; and
a bent loop at the second end of the passer, the passer having a length greater than a combined length of the first and second longitudinal passages.

9. The system of claim 8 wherein the second tunnel member comprises a bone punch that is separable from the guide body and engages the guide body in axial sliding relationship along a second guide axis.

10. The system of claim 9 wherein the guide body further comprises a detent mechanism configured to engage and retain the second tunnel member in a desired axial position relative to the guide body causing the second tunnel member to resist axial movement along the second guide axis.

11. The system of claim 8, wherein the second tunnel member comprises:
a side wall; and
a side opening formed in the side wall nearer the distal end of the second tunnel member than the proximal end of the second tunnel member, the second longitudinal passage extending from the proximal end of the second tunnel member toward the distal end of the second tunnel member and communicating with the side opening.

12. The system of claim 11 wherein the first tunnel member is fixed to the guide body and the first tunnel member comprises a distal opening, the first longitudinal passage communicating with the distal opening, and the side opening formed in the second tunnel member and the distal opening of the first tunnel member are in communication with each other when a first guide axis associated with the distal end of the first tunnel member intersects the side opening;
wherein at least a portion of the first longitudinal passage near the distal end of the first tunnel member is coaxial with the first guide axis.

13. The system of claim 8 wherein the passer further comprises:
a shaft;
a wire extending from the shaft, the shaft extending away from the first end, the shaft having a shaft length, the shaft being relatively rigid compared to the wire, the wire being attached to an end of the shaft and extending away from the shaft to the second end where the wire defines the bent loop, the wire extending from the shaft a wire length, the wire being relatively flexible compared to the shaft; and
an outer tube engaged with the shaft in axial sliding relationship and moveable relative to the shaft from a first position in which the outer tube encloses a portion of the wire length and a second position in which the outer tube encloses less of the wire length.

14. A system for placing a member transosseously through first and second bone tunnels, the system comprising:
a guide body;
a first tunnel member engaged with the guide body, the first tunnel member having:
a proximal end;
a distal end; and
a first longitudinal passage extending through the first tunnel member;
a second tunnel member engaged with the guide body, the second tunnel member having:
a proximal end;
a distal end; and
a second longitudinal passage extending at least partway through the second tunnel member; and
a passer operable to pass a suture from the proximal end of the first tunnel member, through the distal end of the first tunnel member, through the distal end of the second tunnel member, and to the proximal end of the second tunnel member;
wherein the distal end of one of the first tunnel member and the second tunnel member comprises an angled surface that is angled to direct the passer to exit the one of the first tunnel member and the second tunnel member in a direction oriented toward the proximal end of the other of the first tunnel member and the second tunnel member.

15. The system of claim 14 wherein the passer is further operable to pull the suture from the proximal end of the first tunnel member, through the distal end of the first tunnel member, through the distal end of the second tunnel member, and to the proximal end of the second tunnel member.

16. The system of claim 14 wherein the angled surface is further configured to urge the passer, in response to abutment of the passer against the angled surface, to move along the second longitudinal passage.

17. The system of claim 14 wherein the second tunnel member comprises a bone punch that is separable from the guide body and engages the guide body in axial sliding relationship along a second guide axis.

18. The system of claim 14 wherein:
the second tunnel member comprises:
a side wall; and
a side opening formed in the side wall nearer the distal end of the second tunnel member than the proximal end of the second tunnel member, the second longitudinal passage extending from the proximal end of the second tunnel member toward the distal end of the second tunnel member and communicating with the side opening;
the first tunnel member is fixed to the guide body;
the first tunnel member comprises a distal opening;
the first longitudinal passage communicates with the distal opening;
the side opening formed in the second tunnel member and the distal opening of the first tunnel member are in communication with each other when a first guide axis associated with the distal end of the first tunnel member intersects the side opening; and
at least a portion of the first longitudinal passage near the distal end of the first tunnel member is coaxial with the first guide axis.

19. The system of claim 14 wherein the passer comprises:
a first end;

a second end; and a bent loop at the second end of the passer, the passer having a length greater than a combined length of the first and second longitudinal passages.

20. The system of claim 19 wherein the passer further comprises:

a shaft;

a wire extending from the shaft, the shaft extending away from the first end, the shaft having a shaft length, the shaft being relatively rigid compared to the wire, the wire being attached to an end of the shaft and extending away from the shaft to the second end where the wire defines the bent loop at the second end of the passer, the wire extending from the shaft a wire length, the wire being relatively flexible compared to the shaft; and an outer tube engaged with the shaft in axial sliding relationship and moveable relative to the shaft from a first position in which the outer tube encloses a portion of the wire length and a second position in which the outer tube encloses less of the wire length.

* * * * *